(12) United States Patent
Naicker et al.

(10) Patent No.: US 7,060,672 B2
(45) Date of Patent: Jun. 13, 2006

(54) CYCLOSPORIN ANALOG FORMULATIONS

(75) Inventors: Selvaraj A. Naicker, Edmonton (CA); Randall W. Yatscoff, Edmonton (CA); Robert T. Foster, Edmonton (CA)

(73) Assignee: Isotechnika, Inc., Edmonton (CA)

( * ) Notice: Subject to any disclaimer, the term of this patent is extended or adjusted under 35 U.S.C. 154(b) by 170 days.

(21) Appl. No.: 10/274,419

(22) Filed: Oct. 17, 2002

(65) Prior Publication Data

US 2003/0171264 A1 Sep. 11, 2003

Related U.S. Application Data

(60) Provisional application No. 60/370,597, filed on Apr. 5, 2002, provisional application No. 60/346,201, filed on Oct. 19, 2001.

(51) Int. Cl.
*A61K 38/13* (2006.01)
(52) U.S. Cl. ............... 514/2; 514/11; 530/317; 424/439
(58) Field of Classification Search ............... 514/2, 514/11; 424/439; 530/317
See application file for complete search history.

(56) References Cited

U.S. PATENT DOCUMENTS

| | | | |
|---|---|---|---|
| 4,108,985 A | 8/1978 | Rüegger et al. |
| 4,220,641 A | 9/1980 | Traber et al. |
| 4,384,996 A | 5/1983 | Bollinger et al. |
| 4,388,307 A | 6/1983 | Cavanak |
| 4,639,434 A | 1/1987 | Wenger et al. |
| 4,703,033 A | 10/1987 | Seebach |
| 4,764,503 A | 8/1988 | Wenger |
| 4,771,122 A | 9/1988 | Seebach |
| 4,990,337 A | 2/1991 | Kurihara et al. |
| 4,996,193 A | 2/1991 | Hewitt et al. |
| 5,047,396 A | 9/1991 | Orban et al. |
| 5,051,402 A | 9/1991 | Kurihara et al. |
| 5,116,816 A | 5/1992 | Dreyfuss et al. |
| 5,248,499 A | 9/1993 | Czarniecki et al. |
| 5,284,826 A | 2/1994 | Eberle |
| 5,342,625 A | 8/1994 | Hauer et al. |
| 5,350,741 A | 9/1994 | Takada |
| 5,389,382 A | 2/1995 | List et al. |
| 5,474,979 A | 12/1995 | Ding et al. |
| 5,525,590 A | 6/1996 | Bollinger et al. |
| 5,567,592 A | 10/1996 | Benet et al. |
| 5,583,105 A * | 12/1996 | Kovacs et al. ............... 514/11 |
| 5,589,455 A * | 12/1996 | Woo ............... 514/11 |
| 5,603,951 A | 2/1997 | Woo |
| 5,620,971 A | 4/1997 | Armistead et al. |
| 5,635,159 A | 6/1997 | Fu Lu et al. |
| 5,635,161 A | 6/1997 | Adjei et al. |
| 5,639,474 A | 6/1997 | Woo |
| 5,639,724 A | 6/1997 | Cavanak |
| 5,641,745 A | 6/1997 | Ramtoola |
| 5,652,212 A | 7/1997 | Cavanak et al. |
| 5,654,000 A | 8/1997 | Poli et al. |
| 5,656,287 A | 8/1997 | Adler-Moore et al. |
| 5,660,856 A | 8/1997 | Adler-Moore et al. |
| 5,660,858 A | 8/1997 | Parikh et al. |
| 5,670,166 A | 9/1997 | Adler-Moore et al. |
| 5,681,964 A | 10/1997 | Ashton et al. |
| 5,688,525 A | 11/1997 | Adler-Moore et al. |
| 5,693,336 A | 12/1997 | Moynihan |
| 5,719,123 A | 2/1998 | Morley et al. |
| 5,739,105 A | 4/1998 | Kim et al. |
| 5,741,512 A | 4/1998 | Hauer et al. |
| 5,759,566 A | 6/1998 | Poli et al. |
| 5,759,997 A | 6/1998 | Cavanak |
| 5,766,629 A | 6/1998 | Cho et al. |
| 5,767,069 A | 6/1998 | Ko et al. |
| 5,798,333 A | 8/1998 | Sherman |
| 5,827,822 A | 10/1998 | Floc'h et al. |
| 5,834,017 A | 11/1998 | Cho et al. |
| 5,834,019 A | 11/1998 | Gergely et al. |
| 5,843,891 A | 12/1998 | Sherman |
| 5,866,159 A | 2/1999 | Hauer et al. |
| 5,891,845 A | 4/1999 | Myers |
| 5,916,589 A | 6/1999 | Hauer et al. |
| 5,929,030 A | 7/1999 | Hamied et al. |
| 5,945,398 A | 8/1999 | Singh et al. |
| 5,948,755 A | 9/1999 | Barriere et al. |
| 5,952,004 A | 9/1999 | Rudnic et al. |
| 5,958,876 A | 9/1999 | Woo |
| 5,962,014 A | 10/1999 | Hauer et al. |
| 5,962,017 A | 10/1999 | Hauer et al. |
| 5,962,019 A | 10/1999 | Cho et al. |

(Continued)

FOREIGN PATENT DOCUMENTS

| | | |
|---|---|---|
| AU | 752733 | 6/2000 |
| CA | 2185600 | 3/1998 |
| CH | 641356 | 2/1984 |
| DE | 3830494 | 3/1989 |
| DE | 3924207 | 1/1990 |

(Continued)

OTHER PUBLICATIONS

File Promt on STN, AN No: 2000: 109540, Canada's Isotechnika to Test Transplant Drug. Marketletter (Feb. 14, 2000). Abstract only.*

(Continued)

*Primary Examiner*—Anish Gupta
(74) *Attorney, Agent, or Firm*—Fish & Richardson P.C.

(57) ABSTRACT

The present invention relates to formulations containing cyclosporin analogs that are structurally similar to cyclosporin A, in particular isomeric mixtures of cyclosporin analogs that are structurally similar to cyclosporin A. The formulations form stable microemulsion preconcentrates and may provide superior drug bioavailability and/or may reduce one or more adverse effects associated with the administration of cyclosporin. Also disclosed are methods for using and preparing the formulations.

31 Claims, 5 Drawing Sheets

U.S. PATENT DOCUMENTS

Figure 1:
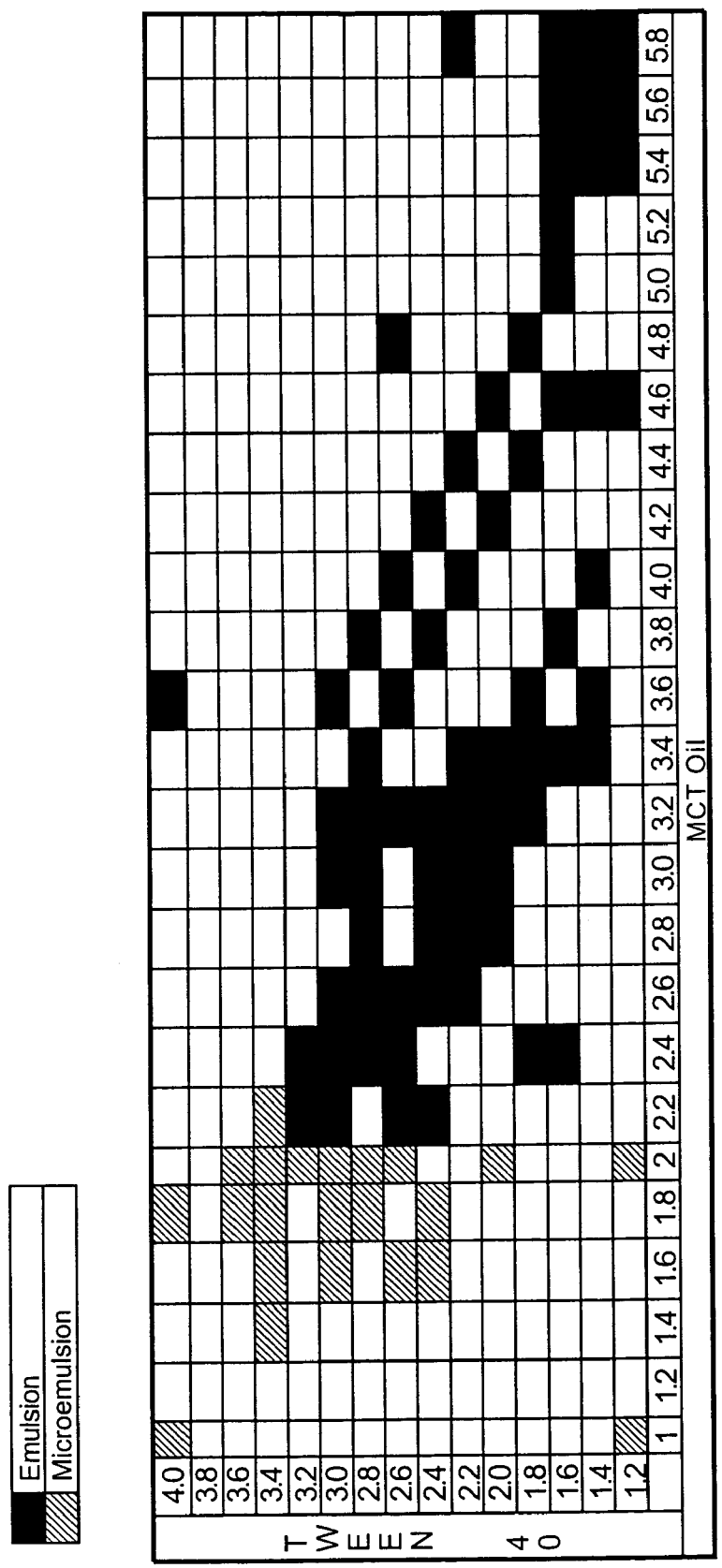

| | | | |
|---|---|---|---|
| 5,965,160 A | 10/1999 | Benita et al. |
| 5,965,527 A | 10/1999 | Barriere et al. |
| 5,977,066 A | 11/1999 | Cavanak |
| 5,977,067 A | 11/1999 | Evers et al. |
| 5,980,939 A | 11/1999 | Kim et al. |
| 5,985,321 A | 11/1999 | Brox et al. |
| 5,994,299 A | 11/1999 | Barriere et al. |
| 5,998,365 A | 12/1999 | Sherman |
| 6,004,580 A | 12/1999 | Backlund et al. |
| 6,004,927 A | 12/1999 | Benet et al. |
| 6,007,840 A | 12/1999 | Hauer et al. |
| 6,008,191 A | 12/1999 | Singh et al. |
| 6,008,192 A | 12/1999 | Al-Razzak et al. |
| 6,022,852 A | 2/2000 | Klokkers et al. |
| 6,024,978 A | 2/2000 | Hauer et al. |
| 6,028,054 A | 2/2000 | Benet et al. |
| 6,028,067 A | 2/2000 | Hong et al. |
| 6,046,163 A | 4/2000 | Stuchlik et al. |
| 6,048,543 A | 4/2000 | Schneider et al. |
| 6,063,762 A | 5/2000 | Hong et al. |
| 6,106,860 A | 8/2000 | Stuchlik et al. |
| 6,113,921 A | 9/2000 | Friedman et al. |
| 6,159,933 A | 12/2000 | Sherman |
| 6,172,107 B1 | 1/2001 | Haeberlin et al. |
| 6,187,745 B1 | 2/2001 | Striker et al. |
| 6,187,747 B1 | 2/2001 | Singh et al. |
| 6,197,335 B1 | 3/2001 | Sherman |
| 6,239,124 B1 | 5/2001 | Zenke et al. |
| 6,254,885 B1 | 7/2001 | Cho et al. |
| 6,258,783 B1 | 7/2001 | Sherman |
| 6,262,022 B1 | 7/2001 | Hauer et al. |
| 6,284,268 B1 | 9/2001 | Mishra et al. |
| 6,306,434 B1 | 10/2001 | Hong et al. |
| 6,306,825 B1 | 10/2001 | Cavanak |
| 6,312,721 B1 | 11/2001 | Stuchlik et al. |
| 6,346,511 B1 | 2/2002 | Singh et al. |
| 6,403,122 B1 | 6/2002 | Andrysek et al. |

FOREIGN PATENT DOCUMENTS

| | | |
|---|---|---|
| DE | 3843241 | 11/1990 |
| DE | 295766 | 11/1991 |
| DE | 4418115 | 12/1994 |
| DE | 19521974 | 12/1996 |
| DE | 10015463 | 10/2001 |
| DE | 10029404 | 1/2002 |
| EP | 0 650 721 | 5/1995 |
| EP | 0 697 214 | 2/1996 |
| EP | 0 760 237 | 3/1997 |
| EP | 0 793 966 | 9/1997 |
| EP | 0 945 136 | 9/1999 |
| EP | 0 539 319 | 12/1999 |
| EP | 0 985 412 | 3/2000 |
| EP | 1 151 755 | 11/2001 |
| GB | 2222770 | 3/1990 |
| GB | 2228198 | 8/1990 |
| GB | 2230440 | 10/1990 |
| GB | 2270842 | 3/1994 |
| JP | 4253907 | 9/1992 |
| JP | 2001122779 | 5/2001 |
| JP | 2001240558 | 9/2001 |
| WO | WO 90/01329 | 2/1990 |
| WO | WO 90/03793 | 4/1990 |
| WO | WO 92/18104 | 10/1992 |
| WO | WO 93/17039 | 9/1993 |
| WO | WO 93/20833 | 10/1993 |
| WO | WO 94/05312 | 3/1994 |
| WO | WO 94/07466 | 4/1994 |
| WO | WO 94/08603 | 4/1994 |
| WO | WO 94/08605 | 4/1994 |
| WO | WO 94/14415 | 7/1994 |
| WO | WO 95/22343 | 8/1995 |
| WO | WO 96/00058 | 1/1996 |
| WO | WO 96/03113 | 2/1996 |
| WO | WO 96/13273 | 5/1996 |
| WO | WO 96/22103 | 7/1996 |
| WO | WO 96/25942 | 8/1996 |
| WO | WO 96/36316 | 11/1996 |
| WO | WO 97/07787 | 3/1997 |
| WO | WO 97/33604 | 9/1997 |
| WO | WO 97/48410 | 12/1997 |
| WO | WO 98/30204 | 7/1998 |
| WO | WO 98/33512 | 8/1998 |
| WO | WO 98/37869 | 9/1998 |
| WO | WO 99/12640 | * 3/1999 |
| WO | WO 01/87324 | 11/2001 |
| WO | WO 02/09762 | 2/2002 |

OTHER PUBLICATIONS

Abel, M.D., et al., "ISATX247: A Novel Calcineurin Inhibitor", *J. Heart Lung Transpl.*, vol. 20, No. 2, p. 161 (2001) Abstract.

Abel, M.D., et al., "ISATX247: A Novel Calcineurin Inhibitor with Minimal Renal Toxcicity", *Am. J. of Transpl.*, vol. 1 (Supp. 1), Abstract No. 1192 (2001).

Abel, M.D., et al., "Phase 1 Evaluation of a Novel Calcineurin Inhibitor ISATX247", *Am. J. of Transpl.*, vol. 1 (Supp. 1), Abstract No. 1319 (2001).

Abel, M.D., et al., "Preclinical Efficacy of a Novel Calcineurin Inhibitor: ISATX247", *Am. J. of Transpl.*, vol. 1 (Supp. 1), Abstract No. 1191, (2001).

Adams, M.W., "d-Alpha Tocopheryl Polyethylene Glycol 1000 Succinate (Eastman Vitamin E TPGS) as an Emulsifier and Bioenhancer for Drugs and Lipoprilic Compounds" Pamphlet by Eastman Chemical Co., (Oct. 1996).

Aspeslet, L., et al., "ISA$_{TX}$247: A Novel Calcineurin Inhibitor", *Transpl. Proc.*, vol. 33, pp. 1048-1051 (2001).

Bennet, W.M., "The Nephrotoxicity of New and Old Immunosuppressive Drugs", *Renal Failure*, vol. 20, pp. 687-690 (1998).

Bestman, H.J., et al., "(Z)-5-Decenyl Accetate, A Sex Attractant for the Male Turnip Moth", *Agnew. Chem. Int. Ed. Engl.*, vol. 17, No. 10, pp. 768-769 (1978).

Biellmann, J.F., et al., Methods of Generation of Heterosubstituted Carbanions, *Organic Reactions*, vol. 27, p. 9(1982).

Birsan, T., et al., "Ex Vivo Evaluation of the Immunosuppressive Effect of the Novel Caldineurin Inhibitor ISATX247 on Whole Blood Lymphocytes of Non-Human Primates", *Am. J. of Transpl.*, 1(Supp. 1), Abstract No. 1199 (2001).

Borok, Z., et al., "Effect of Glutathione Aerosol on Oxidant-Antioxidant Imbalance in Idiopathic Pulmonary Fibrosis", *The Lancet*, vol. 338, p. 215 (Jul. 27, 1991).

Carlsen, H.J., et al., "A Greatly Improved Procedure for Ruthnium Tetroxide Catalyzed Oxidations of Organic Compounds", *J. Org. Chem.*, vol. 46, No. 19, pp. 3936-3938 (1981).

Chang, T., et al., "The Effect of Water-Soluble Vitamin E On Cyclosporine Pharmackinetics in Healthy Volunteers", *Clin. Pharmacol. Ther.*, vol. 59, pp. 297-303 (1996).

Corey, E.J., et al., "Highly Reactive Equivalents of Allylidenetriphenylphosphoranes for the Stereospecific Synthesis of 1, 3-Dienes by Cis-Olefination of Hindered Aldehydes", *Terahedron Letters*, vol. 26, No. 47, pp. 5747-5748 (1985).

Drobitch, R.K., et al., "Therapeutic Drug Monitoring in Saliva", *Clin. Pharm.*, vol. 23, No. 5, pp. 365-379 (1992).

Eberle, M.K., "Synthesis of the Main Metabolite (OL-17) of

Cyclosporin A", *J. Org. Chem.*, vol. 57, pp. 2689-2691 (1992).

Ehlinger, E., et al., "Silicon in Synthesis. 10. The (Trimethylsilyl)allyl AnionL A β-Acyl Anion: Equivalent for the Conversion of Aldehydes and Ketones into γ-Lactones", *J. Am. Chem. Soc.*, vol. 102, No. 15, pp. 5004-5011 (1980).

Fruman, D.S., et al., "Calcineurin Phosphatase Activity in T Lymphocytes Is Inhibited by FK506 and Cyclosporin A", *Proc. Natl. Acad. Sci. USA*, vol. 89, pp. 3686-3690 (1992).

Granelli-Piperno, A., et al., "Lymphokine and Nonlymphokine mRNA Levels in Stimulated Human T Cells: Kinetics, Mitogen Requirements, and Effects of Cyclosporin A" *J. Exp. Med.*, vol. 163, pp. 922-937 (1986).

Hanson, J.R., "2.3 Esthers as the Protecting Groups for Alcohols", *Protecting Groups in Organic Synthesis* Ch. 2, pp. 24-25 (1999).

Herbert, M.F., et al., "Bioavailability of cyclosporin with Concomitant Rifampin Administration is Markedly Less than Predicted by Hepatic Enzyme Induction", *Clin. Pharmacol. Ther.*, vol. 52, pp. 453-457 (1992).

Hoffman, R.W., et al., "Diastereoselective Addition of γ-Alkylthio-Allylboronates to Aldehydes", *Tetrahedron Letters*, vol. 21, pp. 4883-4886 (1980).

Hoffmann, R.W., et al., "Stereoselective Synthesis of Alcohols. 8. Diastereoselective Synthesis of β-Methylhomoallyl Alcohols via Crotylboronates", *J. Org. Chem.*, vol. 46, pp. 1309-1314 (1981).

Hofle, G., et al., "4-Dialkylaminopyridines as Highly Active Acylation Catalysts", *Agnew. Chem. Int. Ed. Engl.*, vol. 17, pp. 569-583 (1978).

Holt, David W., "Cyclosporin and Vitamin E", *The Lancet*, vol. 338, p. 697 (Sep. 14, 1991).

Hudrlik, P.F., et al., "Stereospecific Olefin-Forming Elimination Reactions of β-Hydroxysilanes", *J. Am. Chem., Soc.*, vol. 97, No. 6, pp. 1464-1468 (1975).

Ikeda, Y., et al., "Stereoselective Synthesis of (Z)- and (E)-1,3-Alkadienes from Aldehydes-Using Organotitanium and Lithium Reagents", *Tetrahedron*, vol. 43, No. 4, pp. 723-730 (1987).

Kobel, et al., "Directed Biosynthesis of Cyclosporins", *European J. Appl. Microbiol and Microtechnol*, vol. 14, pp. 237-240 (1982).

Krensky, A.M., et al., "Immunomodulators: Immunosuppressive Agents, Tolerogens and Immunostimulants", *Goodman & Gilman's The Pharmacological Basis of Therapeutics*, Chapter 53, pp. 1463-1470, (Aug. 1991).

Maksymowych, W.P., et al., "Amelioration of Established Collagen-Induced Arthritis by ISATX247: a Novel Calcineurin Inhibitor", *J. of Rheum.*, vol. 28, Supp. 63, p. 93, Abstract W69 (2001).

Maksymowych, W.P., et al., "Prevention and Treatment of Antigen-Induced Arthritis by ISATX247, A Novel Calcineurin Inhibitor", *J. of Rheum.*, vol. 28, Supp. 63, p. 92, Abstract W68 (2001).

Malmsten, M., "Microemulsions in Pharmaceuticals", *Handbook of Microemulsion, Science & Technology*, Chapter 25, pp. 755-771 (1999).

McMurry, J., "19.12 Nucleophilic Addition of Phosphorus Ylides: The Wittig Reaction", in *Organic Chemistry*, 5th Ed., pp. 780-783 (2000).

Oliyai, R., et al., "Kinetics and Mechanisms of Isomerization of Cyclosporin A", Pharmaceutical Research, vol. 9, No. 5, pp. 617-622 (1992).

Peterson, D.J., "A Carbonyl Olefination Reaction Using Silyl-Substituted Organometallic Compounds", *J. Org. Chem.*, pp. 780-784 (1967).

Ramachandran, P.V., et al., eds., "Intromolecular Allylboration Reactions", in *ACS Symposium Series 783, Organoboranes for Synthesis*, pp. 162-164,174 (2001).

Reetz, M.T., "5. Simple Diastereoselectivity", *Organotitanium Reagents in Organic Synthesis*, pp. 148-168 (1986).

Rich, D.H., et al., "Synthesis and Antimitogenic Activities of Four Analogues of Cyclosporin A Modified in the 1-Position", *J. Med. Chem.*, vol. 29, pp. 978-984 (1986).

Roush, W.R., "Allyl Organometallics in Comprehensive Organic Synthesis", *Pergamon Oxford*, vol. 2, pp. 1-53 (1991).

Schreiber, S.L., et al., "The Mechanism of Action of Cyclosporin A and FK506", *Immunol. Today*, vol. 13, pp. 136-142 (1992).

Shapiro, R.J., et al., Prolonged Islet Allograft Survival Without Toxicity Using ISATX247: a Novel Calcineurin Inhibitor, *Am. J. of Transpl.*, vol. 1 (Supp. 1), Abstract No. 828 (2001).

Sketris, I., et al., "Optimizing the Use of Cyclosporine in Renal Transplanation", Clin. Biochemistry, vol. 28, pp. 195-211 (1995).

Smith, M.B., et al., "Stereochemistry: Molecules with More than One Chiral (Sterogenic) Center", *March's Advanced Organic Chemistry, 5th Ed.*, pp. 144-147 (2001).

Smith, M.B., et al., "The Peterson Alkenlation Reaction", *March's Advanced Organic Chemistry, 5th Ed.*, pp. 1228-1229 (2001).

Sokol, R.J., et al., "Improvement of Cyclosporin absorption in Children After Liver Transplantation by Means of Water Soluble Vitamin E", *The Lancet*, vol. 338, pp. 212-214 (1991).

Streitwieser, A., et al., "16.4 Protecting Groups", "16.5 Industrial Syntheses" and 27.3 "Preparation of Diols", *Intro. to Org. Chem.*, 2nd Ed., pp. 475-476 and 844-846, respectively, (1981).

Thliveris, J.A., et al., "Chronic Ciclosporin Nephrotoxicity: A Rabbit Model", *Nephron*, vol. 57, pp. 470-476 (1991).

Thliveris, J.A., et al., "Chronic Cyclosporin-Induced Nephrotoxicity: A Rabbit Model", *Transplantation*, vol. 57, pp. 774-776 (1994).

Thomas, S.E., "Organic Synthesis: the Roles of Boron and Silicon", *Oxford University Press*, pp. 34-35, 67-69 and 85-87 (1991).

Traber, et al., "162. Isolation and Structure Determination of the New Cyclosporins E, F, G, H and I", *Helv. Chim. Acta.* vol. 65, pp. 1655-1677 (1982).

Traber, et al., "122. The Structure of Cyclosporin C", *Helv. Chim. Acta, Helv. Chim. Acta*, vol. 60, pp. 1247-1255 (1977).

Tsai, D.J.S., et al., "A Stereocontrolled Synthesis of (Z) and (E) Terminal Dienes from Pinacol (E)-1-Trimethylsilyl-1-Propene-3-Boronate", *Tetrahedron Letters*, vol. 22, No. 29, pp. 2751-2752 (1981).

Ukai, J., et al., "Direct, Stereoselective Synthesis of Ether E—or—Z-1,3-Dienes", *Tetrahedron Letters*, vol. 24, No. 37, pp. 4029-4032 (1983).

Valantine, H.A., et al., "Recent Advances in Cardiac Transplantation", *N. Eng. J. Med.*, vol. 333, No. 10, pp. 660-661 (1995).

von Wartburg, et al., "Chemistry of the Natural Cyclosporin Metabolites", *Prog. Allergy*, vol. 38, pp. 28-45 (1986).

Wang, et al., "Cyclosporine Nephrotoxicity: Attenuation by an Antioxidant-Inhibitor of Lipid Peroxidation In Vitro and In Vivo", *Transplantation*, vol. 58, pp. 940-946 (1994).

Weidmann, B., et al., "Organometallic Compounds of Titanium and Zirconium as Selective Neucleophilic Reagents in Organic Synthesis", *Agnew. Chem. Int. Ed. Engl.*, vol. 22, pp. 31-45 (1983).

Wenger, R., "Synthesis of Cyclosporine and Analogues: Structure, Activity, Relationships of New Cyclosporine Derivatives", *Transpl. Proc.*, vol. 15, Suppl. 1, pp. 2230-2241 (1983).

Wenger, R.M., "Synthesis of Cyclosporine and Analogues: Structural Requirements for Immunosuppressive Activity", *Angew. Chem. Int. Ed. Engl.*, vol. 24, pp. 77-85 (1985).

Wenger, R.M., "Cyclosporine and Analogues—Isolation and Synthesis—Mechanism of Action and Structural Requirements for Pharmacological Activity", *Progress in the Chemistry of Organic Natural Products*, vol. 50, pp. 123-168 (1986).

Yamamoto, Y., et al., "Selective Reactions Using Allylic Metals" *Chemical Rev.*, pp. 2207-2293 (1993).

Yang, D., et al., "A $C_2$ Symmetric Chiral Ketone for Catalytic Asymmetric Epoxidation of Unfunctionalized Olefins", *J. Am. Chem. Soc.*, vol. 118, pp. 491-492 (1996).

Yang, D., et al., "Novel Cyclic Ketones for Catalytic Oxidation Reactions", *J. Org. Chem.*, vol. 63, pp. 9888-9894 (1998).

Yatscoff, R.W., et al., "ISATX247: Phase 1 Clinical Trial Results of the Novel Calcineurin Inhibitor", *ILAR*, Abstract W133 (2001).

Yatscoff, R.W., et al., "Pharmacokinetics of a Novel Calcineurin Inhibitor: ISATX247." *Therap. Drug. Mon.*, vol. 23, No. 4, p. 496, Abstract 161 (2001).

Yatscoff, R.W., et al., "The Preclinical Evaluation of a Novel Calcineurin Inhibitor: ISATX247", *Therp. Drug. Mon.*, vol. 23, No. 2, p. 487, Abstract 126 (2001).

Yatscoff, R.W., et al., "Phase 1 Clinical Trials Results of ISATX247: A Novel Calcineurin Inhibitor", *Therp. Drug. Mon.*, vol. 23, No. 4, p. 496, Abstract 162 (2001).

"Eastman Vitamin E TPGS", www.eastman.com, Nov. 14, 2002.

\* cited by examiner

CYCLOSPORIN ANALOG FORMULATIONS

CROSS-REFERENCE TO RELATED APPLICATIONS

This application claims priority under 35 U.S.C. 119(e) to U.S. Provisional Application Ser. No. 60/370,597 which was filed on Apr. 5, 2002, and to U.S. Provisional Application Ser. No. 60/346,201 which was filed on Oct. 19, 2001, the disclosures of which are incorporated herein in their entirety.

FIELD OF THE INVENTION

The present invention relates to formulations containing cyclosporin analogs that are structurally similar to cyclosporin A. In particular, the formulations contain isomeric mixtures of the cyclosporin analog $ISA_{Tx}247$. These formulations form stable microemulsions which provide high drug solubility, superior drug bioavailability and may reduce one or more adverse effects associated with the administration of cyclosporin. Also disclosed are methods for using and preparing the formulations.

BACKGROUND OF THE INVENTION

REFERENCES

The following references are referred to by numbers in parentheses at the relevant portion of the specification.
1. Gupta and Robinson, *Treatise on Oral Controlled-drug Delivery*, Text Ed. 1992, edited by Aegis Cadence, Mandel Decker, Inc.
2. Traber et al., *Helv. Chim. Acta,* 60: 1247–1255 (1977)
3. Kobel et al., *Europ. J. Applied Microbiology and Biotechnology,* 14: 237–240 (1982)
4. von Wartburg et al., *Progress in Allergy,* 38: 28–45 (1986)
5. Rich et al. (*J. Med. Chem.,* 29: 978 (1986)
6. U.S. Pat. No. 4,384,996, issued on May 24, (1983)
7. U.S. Pat. No. 4,771,122, issued on Sep. 13, (1988)
8. U.S. Pat. No. 5,284,826, issued on Feb. 8, (1994)
9. U.S. Pat. No. 5,525,590, issued on Jun. 11, (1996)
10. Sketris et al., *Clin. Biochem.,* 28: 195–211 (1995)
11. Bennett, *Renal Failure,* 20: 687–90 (1998)
12. Wang et al., *Transplantation,* 58:940–946 (1994)
13. "Eastman Vitamin E TPGS", Eastman Brochure, Eastman Chemical Co., Kingsport, Tenn. (October 1996)
14. *Hawley's Condensed Chemical Dictionary*, (1987)
15. Ellis, *Progress in Medicinal Chemistry* 25, (1988) Elsevier, Amsterdam
16. Sokol, R. J., *Lancet,* 338(8761): 212, (1991)
17. Sokol, R. J., *Lancet,* 338(8768): 697, (1991)

The disclosure of each of the above publications or patents is hereby incorporated by reference in its entirety to the same extent as if the language of each individual publication and patent were specifically and individually incorporated by reference.

The Use of Cyclosporin as a Therapeutic Agent

Despite efforts to avoid graft rejection through host-donor tissue type matching, in the majority of transplantation procedures, immunosuppressive therapy is critical to the viability of the donor organ in the host. A variety of immunosuppressive agents have been employed in transplantation procedures, including azathioprine, methotrexate, cyclophosphamide, FK-506, rapamycin and corticosteroids. Cyclosporins are finding increasing use in immunosuppressive therapy due to their preferential effect on T-cell mediated reactions (1).

Cyclosporin is a potent immunosuppressive agent that has been demonstrated to suppress humoral immunity and cell-mediated immune reactions such as allograft rejection, delayed hypersensitivity, experimental allergic encephalomyelitis, Freund's adjuvant arthritis and graft versus host disease (GVHD). It is used for the prophylaxis of organ rejection subsequent to organ transplantation, for treatment of rheumatoid arthritis, for the treatment of psoriasis and for the treatment of other autoimmune diseases such as type I diabetes, Crohn's disease and lupus. Many naturally occurring cyclosporins are well known in the art. Non-natural cyclosporins have been prepared by total- or semi-synthetic means or by the application of modified culture techniques. Thus, the class of available cyclosporins is substantial, and includes, for example, the naturally occurring cyclosporins A (CsA) through Z (CsZ), as well as other non-natural cyclosporin derivatives such as dihydro- and iso-cyclosporins (2, 3, 4). CsA analogs containing modified amino acids in the 1-position have been reported by Rich et al.(5). Immunosuppressive, anti-inflammatory and anti-parasitic CsA analogs are described in U.S. Pat. Nos. 4,384,996 (6), 4,771,122 (7), 5,284,826 (8) and 5,525,590 (9), assigned to Sandoz.

Cyclosporin is a lipophilic molecule having a molecular weight of 1202 daltons. Owing to the poor solubility in water and the high lipophilicity of cyclosporin A, pharmaceutical compositions of cyclosporin A with customary solid or liquid pharmaceutical carriers often have disadvantages. For example, the cyclosporins are not satisfactorily absorbed from such compositions, or the compositions are not well tolerated, or they are not sufficiently stable when stored. Often, the dissolved concentration is low in relation to the daily dose.

Adverse Effects of Cyclosporin Therapy

There are numerous adverse effects associated with cyclosporin therapy. These include nephrotoxicity, hepatotoxicity, cataractogenesis, hirsutism, parathesis and gingival hyperplasia (10). The most serious adverse effect is nephrotoxicity.

Acute cyclosporin nephrotoxicity is accompanied morphologically by tubular lesions characterized by inclusion bodies, isometric vacuolation and microcalcification. That leads to a decrease in the glomerular filtration rate, which can be identified by the rapid increase in serum creatinine in patients treated with cyclosporin (11).

The exact mechanism by which cyclosporin causes renal injury is not known. In rat studies, chronic CsA-induced functional and structural deterioration of the kidney was accompanied by renal lipid peroxidation. It has been shown by Wang et al. that co-administration of an anti-oxidant with CsA reduced the renal injury in the rat (12).

Previous attempts in the art to reduce the nephrotoxic risks associated with cyclosporin therapy include the co-administration of the drug with an agent that delays the metabolism of cyclosporin, effectively reducing the dose required to maintain therapeutic blood levels. However, this method often does not resolve the problem of high variation of cyclosporin bioavailability (12). Thus, the problem of preparing a cyclosporin formulation that has excellent bioavailability but which does not cause adverse side effects is well known in the art.

Dosage Forms

In order for a drug to perform its therapeutic activity, a therapeutic amount of the drug must be made bioavailable, i.e., it must be able to get to the site of action in the patient. Oral drug delivery is known in the art, and popular because of ease of administration. However, oral dosage forms are complicated by the fact that the drug must first be released from the dosage form over a given time in the gut, and must be solubilized and absorbed in the gastrointestinal tract. Thus, proper drug release from the dosage form and solubilization of the drug in the gastrointestinal (GI) tract are critical.

Well known oral dosage forms that work well within the confines of the GI tract include tablets, capsules, gel capsules, syrups, suspensions, emulsions, microemulsions and pre-emulsion concentrates. Solubility plays a large role in the development of oral dosage formulations, because the formulation used to deliver the active drug will affect the amount and/or concentration of the drug that reaches the active site over a given period of time. The composition of the formulation also directly affects the solubilization of the drug compound in the gastrointestinal tract, and consequently the extent and rate of the absorption of the active drug compound into the blood stream. In addition, the therapeutic value of a drug is affected by the rate in which the drug is released from the delivery system itself, which in turn affects the rate and extent of solubilization of the active compound in the gastrointestinal tract before absorption (1).

In conventional systems known in the art, drug content is released into the gastrointestinal tract within a short period of time, and plasma drug levels peak at a given time, usually within a few hours after dosing. The design of known oral drug delivery systems, including cyclosporin formulations, is based on obtaining the fastest possible rate of drug dissolution at the risk of creating undesirable, dose related side effects.

Thus, there is a serious need for cyclosporin formulations with reduced toxicity but which retain high levels of bioavailability, and which do not need to be administered with another agent.

SUMMARY OF THE INVENTION

The present invention is based on the discovery that certain formulations, preferably microemulsion preconcentrate and microemulsion formulations, can provide the delivery of the cyclosporin analog, $ISA_{Tx}247$, which reduces one or more of the adverse effects associated with cyclosporin, while maintaining a high bioavailability of the drug. Further, the formulations of the present invention also increases the immunosuppressive effects of $ISA_{Tx}247$ by providing sufficient bioavailability.

The formulations of the present invention all contain $ISA_{Tx}247$ as the active ingredient and synthetic or vegetable oils emulsified with a synthetic co-emulsifier such as a non-ionic surfactant that has a polyoxylated moiety Thus, the present formulations contain $ISA_{Tx}247$, a surfactant, ethanol, a lipophilic and/or an amphiphilic solvent. The formulations of the present invention may be adjusted for pH and isotonicity as needed, and may also include biocompatable polymers such as protective colloids, suspension stabilizers and building agents, excipients, binders and carriers, as needed.

In one preferred aspect, the invention is directed to a microemulsion preconcentrate comprising a) a pharmaceutically effective amount of $ISA_{Tx}247$, b) Vitamin E TPGS, c) MCT oil, d) an emulsifier selected from the group consisting of Tween 40 and Tween 80; and e) ethanol. Preferably the microemulsion preconcentrate comprises from about 5 to about 10% by weight of $ISA_{Tx}247$, greater than 0% to about 50% by weight of Vitamin E TPGS, greater than 0% to about 50% by weight of MCT oil, greater than 0% to about 50% by weight of emulsifier and about 5% to about 15% by weight of ethanol, wherein the formulation is a liquid microemulsion preconcentrate at room temperature. More preferably, the ratio by weight of a:b:c:d:e is about 0.5–1:4:2:2:1.

The present invention also contemplates a method of preparing a microemulsion preconcentrate comprising mixing the MCT oil, the emulsifier, the ethanol, the Vitamin E TPGS, and the proper amount of $ISA_{Tx}247$ until the $ISA_{Tx}247$ is completely dissolved, wherein the formulation is a liquid at room temperature.

In another aspect, the invention is directed to a pharmaceutical formulation comprising a) a pharmaceutically effective amount of $ISA_{Tx}247$, b) Vitamin E $\partial$-α-tocopheryl polyethylene glycol 1000 succinate (Vitamin E TPGS), c) medium chain triglyceride (MCT) oil, d) Tween 40, and e) ethanol. Preferably the pharmaceutical formulation is a microemulsion; more preferably the formulation is a microemulsion preconcentrate. The formulation preferably comprises from about 5 to about 10% by weight of $ISA_{Tx}247$, from about 20 to about 50% by weight of Vitamin E TPGS, from about 5 to about 20% by weight of MCT oil, from about 5% to about 50% of Tween 40 and about 5 to about 15% by weight of ethanol. More preferably, the ratio by weight of a:b:c:d:e is about 0.5–1:4:2:2:1.

In a further aspect, the invention is directed to a method of producing immunosuppression comprising administering to a subject in need thereof an effective amount of the pharmaceutical formulation comprising a) a pharmaceutically effective amount of $ISA_{Tx}247$, b) Vitamin E TPGS, c) MCT oil, d) Tween 40, and e) ethanol.

The present invention also contemplates a method of preparing the pharmaceutical formulation of the present aspect of the invention comprising mixing the MCT oil, the Tween 40, the ethanol, the Vitamin E TPGS, and the proper amount of $ISA_{Tx}247$ until the $ISA_{Tx}247$ is completely dissolved.

In a further aspect, the invention is directed to a pharmaceutical formulation comprising a) a pharmaceutically effective amount of $ISA_{Tx}247$, b) Vitamin E TPGS, c) MCT oil, d) Tween 80, and e) ethanol. Preferably the pharmaceutical formulation is a microemulsion; more preferably the formulation is a microemulsion preconcentrate. The pharmaceutical formulation preferably comprises from about 5% to about 10% by weight of $ISA_{Tx}247$, from about 20% to about 50% by weight of Vitamin E TPGS, from about 5% to about 20% by weight of MCT oil, from about 5% to about 50% by weight of Tween 80 and about 5% to about 15% by weight of ethanol. More preferably, the ratio by weight of a:b:c:d:e is about 0.5–1:2:4:2:1.

In a further aspect, the invention is directed to a method of producing immunosuppression comprising administering to a subject in need thereof an effective amount of the pharmaceutical formulation comprising a) a pharmaceutically effective amount of $ISA_{Tx}247$, b) Vitamin E TPGS, c) MCT oil, d) Tween 80, and e) ethanol.

The present invention also contemplates a method of preparing the pharmaceutical formulation of the present aspect of the invention comprising mixing the MCT oil, the Tween 80, the ethanol, the Vitamin E TPGS, and the proper amount of $ISA_{Tx}247$ until the $ISA_{Tx}247$ is completely dissolved.

In yet a further aspect, the present invention is directed to a pharmaceutical formulation comprising a) a pharmaceutically effective amount of $ISA_{Tx}247$, b) MCT oil, c) Tween 80, d) triacetin, and e) ethanol. Preferably the pharmaceutical formulation is a microemulsion; more preferably the formulation is a microemulsion preconcentrate. The pharmaceutical formulation preferably comprises from about 5% to about 10% by weight of $ISA_{Tx}247$, from about 20% to about 50% by weight of triacetin, from about 5% to about 50% by weight of MCT oil, from about 5% to about 50% by weight of Tween 80 and about 5% to about 15% by weight of ethanol. More preferably, the ratio by weight of a:b:c:d:e is about 0.5–1:5:3:1:1.

In a further aspect, the invention is directed to a method of producing immunosuppression comprising administering to a subject in need thereof an effective amount of the pharmaceutical formulation comprising a) a pharmaceutically effective amount of $ISA_{Tx}247$, b) MCT oil, c) Tween 80, d) triacetin, and e) ethanol.

The present invention also contemplates a method of preparing the pharmaceutical formulation of the present aspect of the invention comprising mixing the MCT oil, the Tween 80, the ethanol, the triacetin, and the proper amount of $ISA_{Tx}247$ until the $ISA_{Tx}247$ is completely dissolved.

In still a further aspect, the invention is directed to a pharmaceutical formulation comprising a) a pharmaceutically effective amount of a) $ISA_{Tx}247$, b) Tween 80, c) Vitamin E TPGS, d) ethanol, and e) isopropyl myristate. Preferably the pharmaceutical formulation is a microemulsion; more preferably, the formulation is a microemulsion preconcentrate. The pharmaceutical formulation preferably comprises from about 5% to about 10% by weight of $ISA_{Tx}247$, from about 20% to about 50% by weight of Vitamin E TPGS, from about 5% to about 55% by weight of isopropyl myristate, from about 5% to about 50% by weight of Tween 80 and about 5% to about 15% by weight of ethanol. More preferably, the ratio by weight of a:b:c:d:e is about 0.5–1:2:1:1:6.

In a further aspect, the invention is directed to a method of producing immunosuppression comprising administering to a subject in need thereof an effective amount of the pharmaceutical formulation comprising a) $ISA_{Tx}247$, b) Tween 80, c) Vitamin E TPGS, d) ethanol, and e) isopropyl myristate.

The present invention also contemplates a method of preparing the pharmaceutical formulation of the present aspect of the invention comprising mixing the isopropyl myristate, the Tween 80, the ethanol, the Vitamin E TPGS n, and the proper amount of $ISA_{Tx}247$ until the $ISA_{Tx}247$ is completely dissolved.

In still a further aspect, the invention is directed to a pharmaceutical formulation preconcentrate comprising a) a pharmaceutically effective amount of $ISA_{Tx}247$, b) Vitamin E TPGS, c) MCT oil, d) Tween 40, and e) ethanol. The pharmaceutical formulation preconcentrate preferably comprises from about 5% to about 10% by weight of $ISA_{Tx}247$, from about 20% to about 50% by weight of Vitamin E TPGS, from about 5% to about 20% by weight of MCT oil, from about 5% to about 50% by weight of Tween 40 and about 5% to about 15% by weight of ethanol. More preferably, the ratio by weight of a:b:c:d:e is about 0.5:4:2:2:1. Even more preferably, the formulation is a microemulsion preconcentrate, wherein the preconcentrate, when mixed with an aqueous media, forms a clear stable microemulsion solution. Preferably, the aqueous media is water or fruit juice, excluding grapefruit juice. In addition, the preconcentrate is preferably mixed with the aqueous media in a ratio of about 1 part preconcentrate to between about 10 and about 100 parts aqueous media.

In a further aspect, the invention is directed to a method of producing immunosuppression comprising administering to a subject in need thereof an effective amount of the pharmaceutical formulation comprising a) a pharmaceutically effective amount of $ISA_{Tx}247$, b) Vitamin E TPGS, c) MCT oil, d) Tween 40, and e) ethanol, mixed into an aqueous media.

The present invention also contemplates a method of preparing the pharmaceutical formulation of the present aspect of the invention comprising mixing the MCT oil, the Tween 40, the ethanol, the Vitamin E TPGS n, and the proper amount of $ISA_{Tx}247$ until the $ISA_{Tx}247$ is completely dissolved. The resulting preconcentrate is then mixed with aqueous media, preferably in a ratio of about 1 part preconcentrate to about 10 to about 100 parts media.

In yet another aspect, the invention is directed to a pharmaceutical formulation comprising: a) a pharmaceutically effective amount of $ISA_{Tx}247$, b) Vitamin E TPGS, c) MCT oil, d) Tween 40, and e) ethanol. The pharmaceutical formulation may be administered parenterally, such as subcutaneously (SC) or intramuscularly (IM) and is optionally sterilized.

In another aspect of the present invention any one of the microemulsion preconcentrate formulations maybe mixed with an aqueous media to form a clear thermodynamically stable microemulsion solution. The aqueous media may be water or fruit juice, excluding grapefruit juice, which may react adversely with the $ISA_{Tx}247$. In addition, the preconcentrate may be mixed with the aqueous media in a ratio of about 1 part preconcentrate to between about 10 and about 100 parts aqueous media.

In yet another aspect of the present invention, any one of the microemulsion preconcentrate formulations maybe an oral formulation, preferably encapsulated in a soft gelatin capsule.

BRIEF DESCRIPTION OF THE DRAWINGS

FIG. 1 shows a table for the formation of microemulsion preconcentrates as a function of exeipient ratio for Tween 40 and MCT Oil.

FIG. 2 shows a graph providing a comparison of pharmacokinetic (PK) profiles for our $ISA_{TX}247$ microemulsion in comparison with Neoral® in Beagle dogs.

FIG. 3 shows an overview of exemplary synthetic pathways that may be used to prepare the cyclosporin analogs of the present invention, where stereoselective pathways are grouped according to reactive conditions;

FIG. 4 illustrates a synthetic pathway that produces a mixture of (E) and (Z)-isomers of $ISA_{TX}247$ from a bromine precursor;

FIG. 5 illustrates another synthetic pathway that produces a mixture of (E) and (Z)-isomers of $ISA_{TX}247$ from an aldehyde precursor;

DETAILED DESCRIPTION OF THE INVENTION

In general, the terms in the present application are used consistently with the manner in which those terms are understood in the art.

The terms "cyclosporin" and "cyclosporine" are simply a variation in spelling and are used herein interchangeably to refer to the same compound, for example cyclosporin A and cyclosporine A are the same compound) or the same class of compounds, as appropriate.

By the term "microemulsion preconcentrate", as used herein, is meant a system capable upon contact with an aqueous media of providing a microemulsion. The term microemulsion is used herein in its conventionally accepted sense as a non-opaque (clear) or substantially non-opaque thermodynamically stable colloidal dispersion comprising water and organic components including hydrophobic (lipophilic) organic components.

The term "emulsion" is a heterogeneous system, consisting of at least one immiscible liquid intimately dispersed in another in the form of droplets, whose diameters, in general, exceed 0.1 mm. Such systems possess a minimal stability, which may be accentuated by additives such as surface-active agents, finely divided solids, etc. Conventional "emulsions", unlike the microemulsions of the present invention, are considered to be thermodynamically unstable dispersions.

A. Preparation of Formulations

The formulations of the present invention all contain $ISA_{Tx}247$ as the active ingredient and synthetic or vegetable oils emulsified with a coemulsifier, preferably a synthetic co-emulsifier such as a non-ionic surfactant that has a polyoxylated moiety. The formulations of the present invention may be adjusted for pH and isotonicity as needed. The formulations of the present invention may also include biocompatable polymers such as protective colloids, suspension stabilizers and building agents, excipients, binders and carriers, as needed. Certain preferred embodiments form clear stable formulations providing relatively high drug solubility and relatively quick dissolution in aqueous media (less than about 5 minutes with stirring) to form clear microemulsions.

Thus, the present formulation is a microemulsion, or a microemulsion preconcentrate, containing $ISA_{Tx}247$, a surfactant, an oil, ethanol, and an emulsifier that is either a lipophilic and/or an amphiphilic solvent. In certain embodiments, the preparation comprises from about 5% to about 10% by weight of $ISA_{Tx}247$, from about 20% to about 50% by weight of a surfactant, such as tocopheryl polyethylene glycol carboxylic acid ester (or, optionally, emulsion stabilizers such as triacetin) from about 5% to 20% by weight of an oil component, such as MCT oils or isopropyl myristate, from about 5% to about 15% by weight of ethanol, and from about 20% to about 40% by weight of a lipophilic solvent and/or from about 10% to about 55% by weight of an amphiphilic solvent. In addition, the formulation may optionally contain from about 10% to about 20% by weight of another surfactant.

Figure 2:
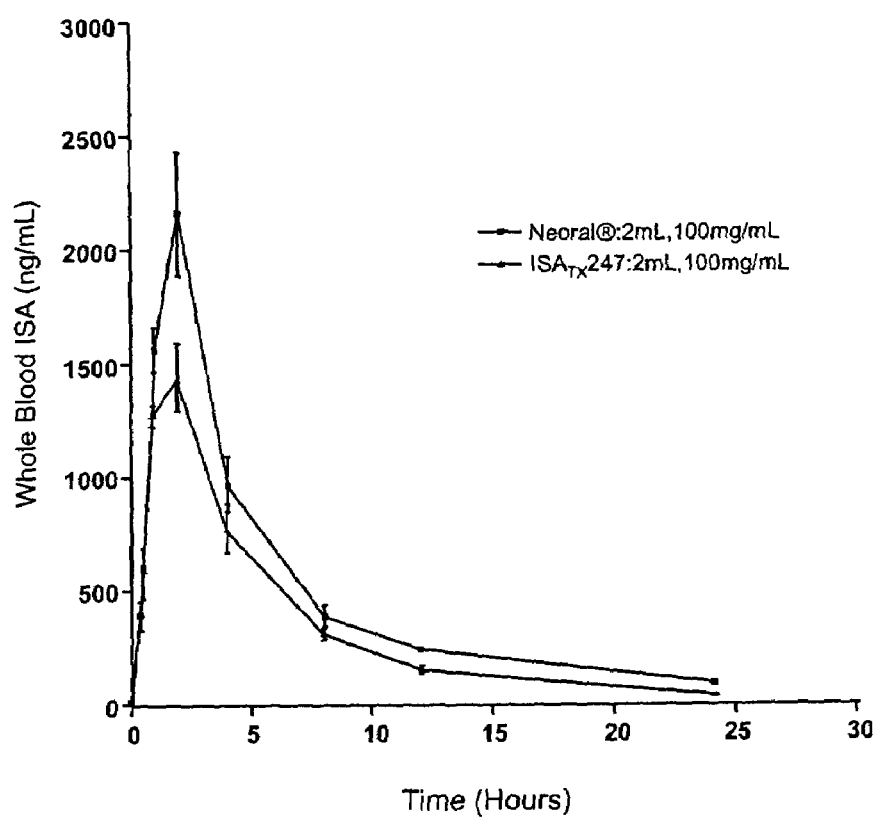

Embodiments of the present invention may have sufficient drug bioavailability (see Tables 3 and 5 and FIG. 2) and/or decreased toxicity (see Tables 5 and 7). The mechanisms for this increased bioavailability and/or decreased toxicity are unknown. However, without being limited by theory, Vitamin E TPGS may contribute to these features of the formulation. For example, co-administration of Vitamin E TPGS has been shown to increase the bioavailability of cyclosporin after liver transplants in children (16, 17).

Active Ingredient

The preferred active ingredient of the formulations of the present invention is an analog of cyclosporin, $ISA_{Tx}247$. $ISA_{Tx}247$ may be present in the formulation as a mixture of E- and Z-isomer or as a single E- or Z-isomer. The structural formulas of the $ISA_{Tx}247$ isomers are as follows:

E-isomer

Z-isomer

The present formulations are composed of the drug $ISA_{Tx}247$, a synthetic or vegetable oil, preferably MCT (medium chain triglycerides) oil emulsified with a synthetic co-emulsifier such as a non-ionic surfactant that has a polyoxyethylated moiety, preferably polyoxyethylated Vitamin E. The formulated content can be adjusted for pH and isotonicity as needed. These formulations can also include biocompatible polymers such as poly(vinyl pyrrolidone) (PVP), poly vinyl alcohol (PVA) or polyethylene glycol (PEG) and other polymers as protective colloids and suspension or bulking agents, excipients, binders and/or carriers, as appropriate.

Figure 3:
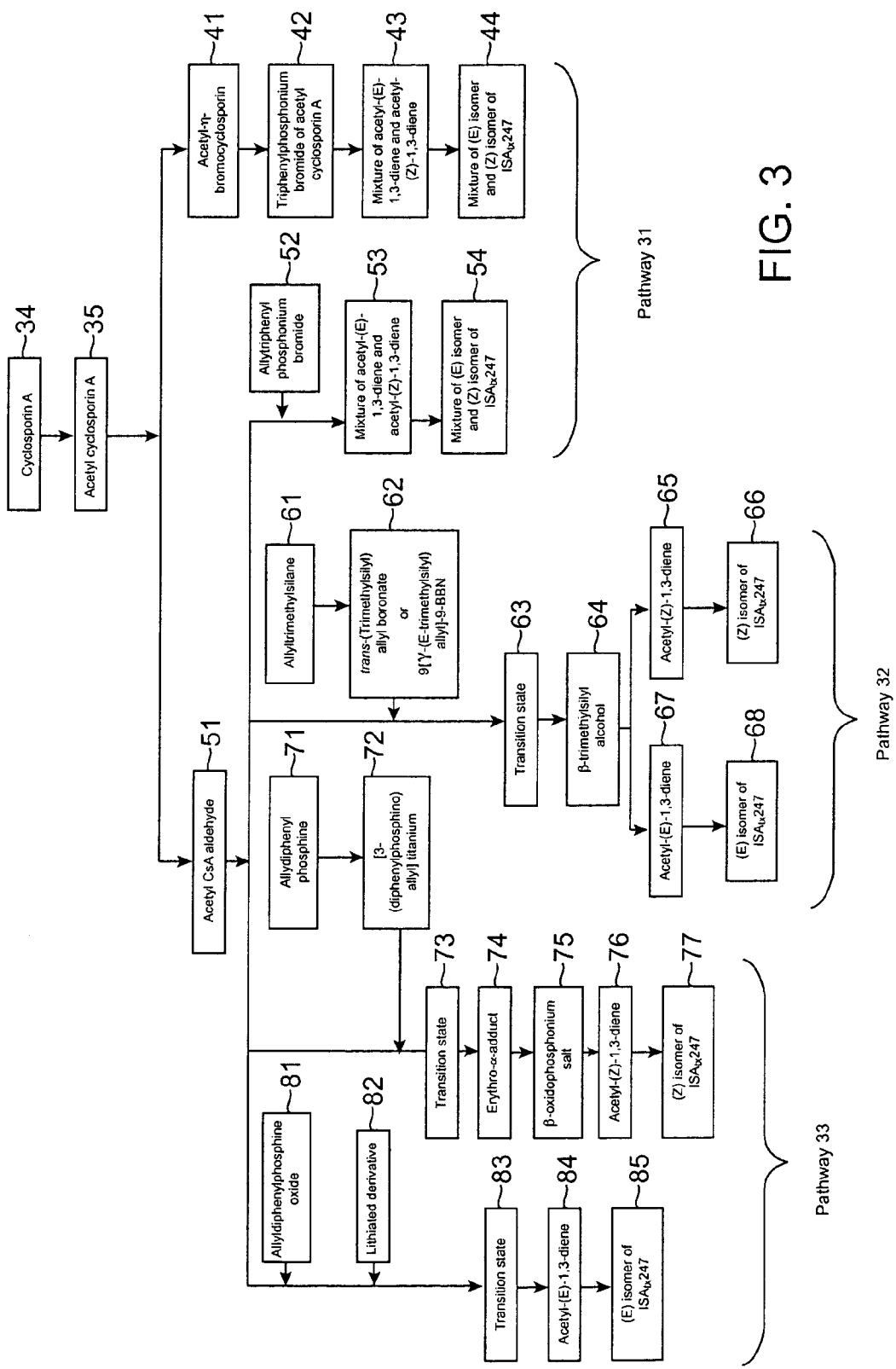

Synthesis of Mixtures of the (F) and (Z)-isomers of $ISA_{Tx}247$ via the Wittig Reaction Wittig reaction pathways exemplified herein are identified by the reference numeral 31 in FIG. 3. Method 1 proceeds through the bromine intermediate acetyl-η-bromocyclosporin 41, whereas method 2 utilizes the aldehyde acetyl cyclosporin A aldehyde 51 as a starting point. The exemplary methods described below utilize a Wittig reaction to introduce an alkene functionality with a mixture of stereochemical configurations.

The Wittig reactions used in the exemplary embodiments disclosed herein to synthesize mixtures of the (E) and (Z)-isomers of $ISA_{Tx}247$ may optionally be carried out in the presence of a lithium halide. The presence of lithium halides in Wittig reactions is well known to have an effect on the ratio of geometrical isomers produced, and therefore the addition of such a compound can aid in producing a desired mixture of the (E) and (Z)-isomers of $ISA_{Tx}247$.

Method 1

Figure 4:
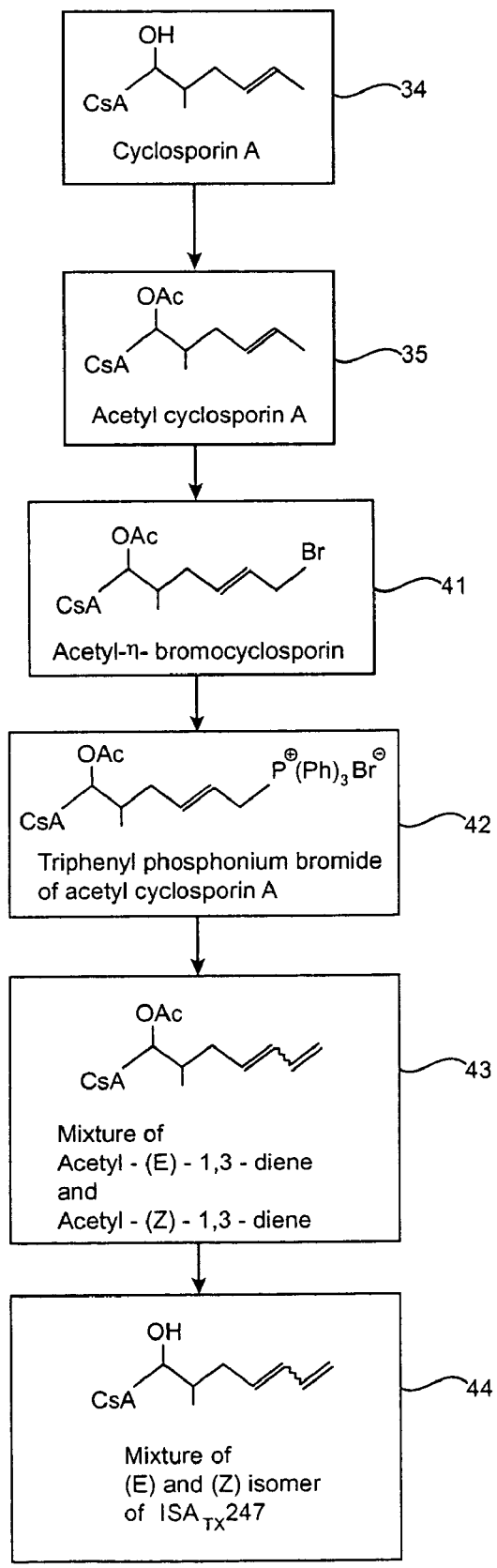

In one embodiment of the present invention, a mixture of (E) and (Z)-isomers of $ISA_{TX}247$ is prepared as shown in FIG. 4. The use of the wavy-lined representation in FIG. 4 (see especially compounds 43 and 44) is meant to denote that the exemplary reaction sequence produces a mixture of (E) and (Z)-isomers. In one embodiment the percentage ratio of the (E) to (Z)-isomers produced ranges from about 10 to 90 percent of the (E)-isomer to about 90 to 10 percent of the (Z)-isomer, but these ranges are only exemplary, and many other ranges are possible. For example, the mixture may contain from about 15 to 85 percent by weight of the (E)-isomer and about 85 to 15 percent of the (Z)-isomer. In other embodiments, the mixture contains about 25 to 75 percent by weight of the (E)-isomer and about 75 to 25 percent by weight of the (Z)-isomer; about 35 to 65 percent by weight of the (E)-isomer and about 65 to 35 percent by weight of the (Z)-isomer; and about 45 to 55 percent by weight of the (E)-isomer and about 55 to 45 percent of the (Z)-isomer. In still another embodiment, the isomeric mixture is an $ISA_{TX}247$ mixture which comprises about 45 to 50 percent by weight of the (E)-isomer and about 50 to 55 percent by weight of the (Z)-isomer. These percentages by weight are based on the total weight of the composition, and it will be understood that the sum of the weight percent of the (E) isomer and the (Z) isomer is 100 weight percent. In other words, a mixture might contain 65 percent by weight of the (E)-isomer and 35 percent by weight of the (Z)-isomer, or vice versa.

Referring to FIG. 4, the terminal η-carbon of the side chain of the 1-amino acid residue of acetyl-cyclosporin A is brominated in the next step of the reaction by refluxing acetyl cyclosporin A 35 with N-bromosuccinimide and azo-bis-isobutyronitrile in a solvent such as carbon tetrachloride, producing the intermediate acetyl-η-bromocyclosporin A 41. N-bromosuccinimide is a reagent that is often used to replace allylic hydrogens with bromine, and it is believed to do so via a free radical mechanism. The preparation of the intermediate 41 was essentially described by M. K. Eberle and F. Nuninger in "Synthesis of the Main Metabolite (OL-17) of Cyclosporin A," *J. Org. Chem.*, Vol. 57, pp. 2689–2691 (1992).

The novel intermediate triphenylphosphonium bromide of acetyl cyclosporin A 42 may be prepared from acetyl-η-bromocyclosporin A 41 by heating the latter compound with triphenylphosphine in a solvent such as toluene.

The novel intermediate 42, and others like it, are contemplated to be key intermediates in the synthesis of a plurality of cyclosporin A analogs that contain a conjugated diene system in the 1-amino acid residue. For example, in addition to triphenylphosphine, compounds such as triarylphosphines, trialkylphosphines, arylalkylphosphines, and triarylarsines may be reacted with acetyl-η-bromocyclosporin A 41 to prepare other activated compounds similar to 42.

Referring again to FIG. 4, a mixture of the (E) and (Z)-isomers of acetyl-1,3-diene 43 may be prepared by stirring the triphenylphosphonium bromide of acetyl cyclosporin A 42 with an excess of formaldehyde in toluene at room temperature. Following addition of the formaldehyde, a base such as sodium hydroxide is added dropwise, and the isomeric mixture of dienes is extracted with ethyl acetate.

Numerous organic chemistry textbooks describe the Wittig reaction. One description in particular is provided by J. McMurry, *Organic Chemistry*, 5$^{th}$ Ed. (Brooks/Cole, Pacific Grove, 2000), pp. 780–783. A Wittig reaction may be used to convert a ketone or an aldehyde to an alkene. In such a process, a phosphorus ylide, also called a phosphorane, may be reacted with the aldehyde or ketone to give a dipolar intermediate called a betaine. Typically the betaine intermediate is not isolated; rather, it spontaneously decomposes through a four-membered ring to yield an alkene and triphenylphosphine oxide. The net result is a replacement of the carbonyl oxygen atom by the $R_2C=$ group originally bonded to the phosphorus.

It will be appreciated by those skilled in the art that a wide variety of reagents may be substituted for the exemplary Wittig reaction reagents cited above. For example, numerous alkyl, aryl, aldehyde, and ketone compounds may be substituted for formaldehyde to prepare a vast number of cyclosporin derivatives. Applicants have carried out the above synthesis with formaldehyde, and in place of formaldehyde, compounds such as acetaldehyde, deuterated formaldehyde, deuterated acetaldehyde, 2-chlorobenzaldehyde, benzaldehyde, and butyraldehyde. Such Wittig reactions may be carried out with compounds other than triphenylphosphonium derivatives, such as triarylphosphines, trialkylphosphines, arylalkylphosphines and triarylarsines. Instead of using sodium hydroxide, various other bases such as sodium carbonate, butyllithium, hexyllithium, sodium amide, lithium hindered bases such as lithium diisopropylamide, and alkali metal alkoxides may be used. In addition to varying these reagents, the reaction may be conducted in various organic solvents or mixtures of organic solvents and water, in the presence of various salts, particularly lithium halides, and at varying temperatures. All of the factors listed above can reasonably be selected by one of ordinary skill in the art to have the desired effect on the stereochemistry of the formed double bond; i.e., the desired effect on the ratio of the cis to trans-isomers.

In a final step of this synthesis, the protecting group on the β-carbon is removed using the following procedure. The mixture of acetyl-(E)-1,3-diene and acetyl-(Z)-1,3-diene 43 is dissolved in methanol, and then water is added. A base such as potassium carbonate is added, and the reaction mixture stirred at room temperature. Bases other than potassium carbonate that may be used include sodium hydroxide, sodium carbonate, sodium alkoxide, and potassium alkoxide. Ethyl acetate is then used to extract the final product mixture of (E) and (Z)-isomers of $ISA_{TX}247$ 44.

Method 2

Figure 5:
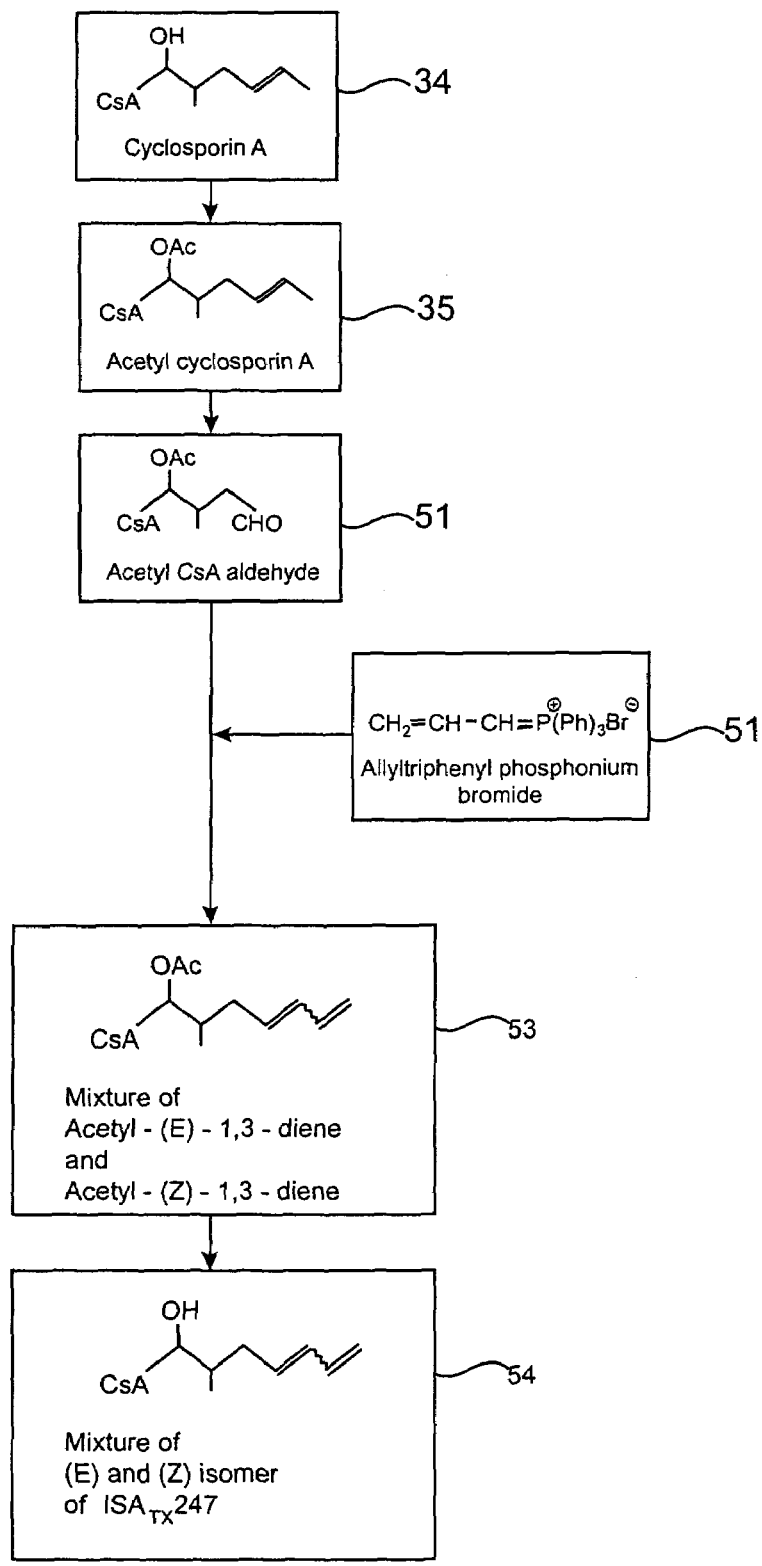

In an alternative reaction pathway for synthesizing a mixture of (E) and (Z)-isomers of $ISA_{TX}247$ via a Wittig reaction strategy, a four step synthetic pathway may be employed as follows: 1) protection of the β-alcohol, as in method 1,2) oxidation of the acetyl-cyclosporin A produced from the first step to produce an aldehyde; 3) a Wittig reaction; and 4) de-acetylation of the Wittig reaction product, or equivalently, hydrolysis of the acetate ester to retrieve the alcohol. This reaction sequence is illustrated in FIG. 5.

This synthetic pathway begins in a manner similar to the Wittig reaction pathway of FIG. 4 in that the first step protects the β-alcohol with an acetate ester group. The two pathways differ from here on, however, in that the next step of method 2 converts acetyl-cyclosporin A 35 to an aldehyde, acetyl cyclosporin A aldehyde 51. This reaction uses an oxidizing agent sufficiently strong to cleave a C=C bond to produce two fragments. Alkene cleavage is known in the art. Ozone is perhaps the most commonly used double bond cleavage reagent, but other oxidizing reagents such as potassium permanganate ($KMnO_4$) or osmium tetroxide can cause double bond cleavage as well.

The use of ruthenium based oxidizing agents has been discussed by H. J. Carlsen et al. in "A Greatly Improved Procedure for Ruthenium Tetroxide Catalyzed Oxidations of Organic Compounds," *J. Org. Chem.*, Vol. 46, No. 19, pp 3736–3738 (1981). Carlsen et al. teach that, historically, the expense of ruthenium metal provided an incentive for the development of catalytic procedures, the most popular of which used periodate or hypochlorite as stoichiometric oxidants. These investigators found a loss of catalytic activity during the course of the reaction with the conventional use of ruthenium which they postulated to be due to the presence of carboxylic acids. The addition of nitrites to the reaction mixture, especially acetonitrile, was found to significantly enhance the rate and extent of the oxidative cleavage of alkenes in a $CCl_4/H_2O/IO_4^-$ system.

According to one embodiment of the present invention, acetyl cyclosporin A aldehyde 51 may be produced from acetyl cyclosporin A 35 by dissolving it in a mixture of acetonitrile and water, and then adding first sodium periodate and then ruthenium chloride hydrate. The aldehyde 51 may be extracted with ethyl acetate. It should be noted that the synthesis of the aldehyde 51 by this oxidative cleavage strategy is important to many of the stereoselective pathways.

The third step of method 2 involves converting the aldehyde 51 to a mixture of (E) and (Z) dienes via a Wittig reaction, in a similar fashion to that of method 1. As in method 1, a phosphorus ylide adds to the aldehyde to yield a betaine (which is not isolated), with the net result that the carbonyl oxygen atom of the aldehyde is replaced by the $R_2C=$ group originally bonded to phosphorus. Again, such Wittig reactions may be carried out with phosphorus containing compounds other than triphenylphosphonium derivatives, such as triarylphosphines, trialkylphosphines, arylalkylphosphines and triarylarsines, at various temperatures, and using a variety of basic solutions and solvents or the addition of various inorganic salts may be used to influence the stereochemistry of the newly formed double bond.

In one embodiment, acetyl cyclosporin A aldehyde 53 is dissolved in toluene, to which is added a base such as sodium hydroxide in water. Allyl triphenylphosphonium bromide 52 is then added, and the reaction stirred for some time. Workup of the product mixture of acetyl (E) and (Z)-1,3-dienes 53 involves extraction with hexane and/or ethyl acetate, where the term "workup" is intended to mean the process of extracting and/or isolating reaction products from a mixture of reactants, products, solvent, etc.

In a final step of method 2, similar to the final step of method 1, the acetate ester group protecting the alcohol at the β-carbon position is removed with potassium carbonate, yielding a mixture of (E) and (Z) isomers of $ISA_{TX}247$ 54. Bases other than potassium carbonate that may be used to remove the protecting group include sodium hydroxide, sodium carbonate, sodium alkoxide, and potassium alkoxide.

Vitamin E TPGS

Tocopheryls are used in the formulations as antioxidants. D-α-tocopheryl polyethylene glycol 1000 succinate (Vitamin E TPGS) (Eastman Kodak, Rochester, N.Y.) is a water soluble derivative of Vitamin E, and has a dual nature of hydrophilicity and lipophilicity and has been used as an antioxidant or as a preservative in formulations known in the art. When used as an antioxidant, tocopheryl or Vitamin E TPGS may be present in from about 0.5% to about 1%, and not more than 5% percent by weight.

Vitamin E TPGS is miscible in water and forms solutions with water at concentrations up to approximately 20% weight, beyond which liquid crystalline phases may form. Vitamin E TPGS has a high degradation temperature and good thermal stability. Micelles are formed at 0.02 percent weight. When Vitamin E TPGS concentration is above 20 percent weight, higher viscosity liquid crystalline phases form. With increasing Vitamin E TPGS concentration in water, more complex liquid crystalline phases evolve from isotropic globular micellar to isotropic cylindrical micellar and hexagonal, hexagonal, mixed hexagonal and reversed hexagonal, reversed globular micellar, and to the lamellar phase (13). In these formulations, Vitamin E TPGS is useful as a surface active agent or as an emulsifier. It may also be used in complex formulations that include a number of other excipients that function as solvent, binder, and filler.

In addition, the Vitamin E TPGS in the present invention may be present not only as an emulsifying agent and adjuvant, but also to inhibit the alteration of the oil, preventing them from becoming rancid.

Oil Component

The oil component of the present formulations may be a vegetable oil, a synthetic oil, an oil substitute such as triacetin, a mineral oil or a medium chain triglyceride (MCT) oil, i.e., a triglyceride oil in which the carbohydrate chain has 8–10 carbon atoms. Preferably, the oil component is MCT oil.

MCT oil has many advantages over vegetable oil, including: 1) a lower susceptibility to oxidation; 2) a specific density of about 0.94–0.95 which is higher than that of vegetable oil and which is close to that of water thus facilitating the obtaining of a stable microemulsion; 3) it is less hydrophobic than vegetable oil and therefore enables the achievement of higher concentrations of the drug dissolved therein; and 4) it has a lower viscosity which enables obtaining a higher concentration of the oily phase in the composition without substantially increasing its viscosity (15).

MCT oil is available commercially. Examples of MCT oils contemplated by the present invention include, but are not limited to, TCR™ (trade name of Societe Industrielle des Oleagineaux, France, for a mixture of triglycerides wherein about 95% of the fatty acid chains have 8 or 10 carbons) and MIGLYOL 812™ (trade name of Dynamit Nobel, Sweden, for a mixed triester of glycerine and of caprylic and capric acids). Isopropyl myristate is another commercially available oil useful in formulations of the present invention.

Examples of vegetable oils contemplated by the present invention include, but are not limited to, soybean oil, cotton seed oil, olive oil, sesame oil and castor oil. Mineral oils include, but are not limited to, natural hydrocarbons or their synthetic analogs. Oily fatty acids, such as oleic acid and linoleic acid, fatty alcohols, such as oleyl alcohol, and fatty esters, such as sorbitan monooleate and hydrophobic sucrose esters, may be used as the oil component, although these are not as preferred as the other oils mentioned herein. Other lipids which may be used in the formulations of the present invention include, but are not limited to, synthetic and semi-synthetic mono-, di- and/or triglycerides, triglycerides prepared by solvent or thermal fractionation of natural, synthetic or semisynthetic triglycerides, and triglycerides prepared by interesterification and/or directed or random rearrangement.

Emulsifiers

The formulations of the present invention contain at least one emulsifier. Preferably the emulsifier or surfactant is a non-ionic lipophilic solvent or a non-ionic amphiphilic solvent; The emulsifier may be a Tween, such as Tween 40, Tween 80, or the like. However, any surfactant capable of forming and microemulsion preconcentrate maybe used. Some examples are given below.

The surfactant component may comprise amphiphilic, hydrophilic or lipophilic surfactants, or mixtures thereof. Especially preferred are non-ionic hydrophilic and non-ionic lipophilic surfactants. Examples of suitable hydrophilic surfactants for use as surfactant components are reaction products of natural or hydrogenated vegetable oils and ethylene glycol. Such products may be obtained in known manner, e.g. by reaction of a natural or hydrogenated castor oil or fractions thereof with ethylene oxide, with optional removal of free polyethyleneglycol components from the product. Also suitable are various tensides, or surfactants, available under the trade name Cremophor™ (polyoxyl castor oil). Particularly suitable is Cremophor™ RH 40 and Cremophor™ EL.

Other examples include polyoxyethylene-sorbitan-fatty acid esters, e.g., mono- and trilauryl, palmityl, stearyl and oleyl esters e.g., Tweens, including polyoxyethylene(20) sorbitanmonolaurate [Tween® 20], polyoxyethylene(20) sorbitanmonopalmitate [Tween® 40], polyoxyethylene(20) sorbitanmonostearate [Tween® 60], polyoxyethylene(20) sorbitanmonooleate [Tween® 80], polyoxyethylene(20)sorbitantristearate [Tween® 65], polyoxyethylene(20)sorbitantrioleate [Tween® 85], polyoxyethylene(4) sorbitanmonolaurate [Tween® 21], polyoxyethylene(4) sorbitanmonostearate [Tween® 61], and polyoxyethylene(5) sorbitanmonooleate [Tween® 81]. Especially preferred products of this class for use in the compositions of the invention are Tween 40 and Tween 80, polyoxyethylene fatty acid esters, such as polyoxyethylene stearic acid esters, polyoxyethylene-polyoxypropylene co-polymers, polyoxyethylene-polyoxypropylene block co-polymers, e.g. of the type known and commercially available under the trade name Poloxamerm, dioctylsuccinate, dioctylsodiumsulfosuccinate, di-2-ethylhexyl-succinate or sodium lauryl sulfate, and phospholipids, in particular, lecithins. Lecithins suitable for use in the compositions of the invention include, but are not limited to, soya bean lecithins. Other suitable products include Cremophor TM, Nikkol TM, glycolated natural or hydrogenated vegetable oils, and caprylic-capric acid diester. Propylene glycol mono- and di-fatty acid esters such as propylene glycol dicaprylate, propylene glycol dilaurate, propylene glycol hydroxystearate, propylene glycol isostearate, propylene glycol laurate, propylene glycol ricinoleate, propylene glycol stearate are also suitable.

The formulations of the present invention may further comprise a pharmaceutically acceptable surfactant, colloid, suspension, bulking agent, excipient, carrier, tenside or cotenside.

B. Preferred Formulations of the Present Invention

Embodiments of the present invention are preferably stable microemulsion preconcentrates which provide sufficient drug bioavailability and/or reduced toxicity. These formulations may have superior ability to increase drug bioavailability and to reduce adverse effects associated with the administration of cyclosporin and its analogs. Microemulsion formulations allow for delivery of a drug in smaller particles. Delivery of a unit dosage of a drug in smaller particles allows for increased surface area and presumably higher absorption and better bioavailability. Microemulsions are known in the art. However, microemulsions using the components of the present formulation are formed by the judicious choice of ratios of ethanol, Vitamin E TPGS, oil component, and emulsifier which are outside the ranges of previous known formulations for active agents similar to $ISA_{Tx}247$. Compositions containing less than 5% of ethanol, or greater than 50% of Vitamin E TPGS form solid microemulsion preconcentrates at room temperature, which is a less preferred embodiment of the formulations of this invention.

The relative proportion of ingredients in the compositions of the invention will, of course, vary considerably depending on the particular type of composition concerned, e.g. whether it is a "microemulsion preconcentrate", microemulsion, regular emulsion, solution and so forth. The relative proportions will also vary, depending on the particular function of ingredients in the composition, for example, in the case of a surfactant component of a "microemulsion preconcentrate", on whether this is employed as a surfactant only or both a surfactant and a co-solvent. The relative proportions will also vary depending on the particular ingredients employed and the desired physical characteristics of the product composition. Determination of workable proportions in any particular instance will generally be within the capability of the skilled artisan. All indicated proportions and relative weight ranges described below are accordingly to be understood as being indicative of preferred or individually inventive teachings only and not as not limiting the invention in its broadest aspect. The microemulsions of the present inventions may be microemulsion preconcentrates. Preferred formulations of the present invention are as follows:

Formulation 1
a) a pharmaceutically effective amount of $ISA_{Tx}247$;
b) Vitamin E TPGS;
c) MCT oil;
d) Tween 40; and
e) ethanol
in a ratio of ingredients of 0.5–1:4:2:2:1.

Formulation 2
a) a pharmaceutically effective amount of $ISA_{Tx}247$;
b) Vitamin E TPGS;
c) MCT oil;
d) Tween 80; and
e) ethanol
in a ratio of ingredients of 0.5–1:2:4:2:1.

Formulation 3
a) a pharmaceutically effective amount of $ISA_{Tx}247$;
b) MCT oil;
c) Tween 80;
d) triacetin; and
e) ethanol
in a ratio of ingredients of 0.5–1:5:3:1:1.

Formulation 4
a) a pharmaceutically effective amount of $ISA_{Tx}247$;
b) Tween 80;
c) Vitamin E TPGS;
d) ethanol; and
e) isopropyl myristate
in a ratio of ingredients of 0.5–1:2:1:1:6.

Formulation 5
a) a pharmaceutically effective amount of $ISA_{Tx}247$;
b) Vitamin E TPGS;
c) MCT oil;
d) Tween 40; and
e) ethanol in a ratio of ingredients of 0.5–1:4:2:2:1, with the formulation further mixed with an aqueous medium to form a clear stable microemulsion solution. Aqueous media may include, but are not limited to water, fruit juices, such as apple juice, tea, milk and cocoa. Useful fruit juices, exclude grapefruit juice and preferably include apple juice. The formulation is preferably dissolved into the aqueous media at a ratio of about 1 part formulation to about 10 to about 100 parts aqueous media.

The pharmaceutical formulations of the present invention preferably allow for sufficient bioavailability. Preferably, the bioavailability of $ISA_{Tx}247$ is equal to or greater than 30%, more preferably the bioavailability is greater than 40%. The pharmaceutical formulations are preferably in a form for oral administration, such as microemulsions, or microemulsion preconcentrates. The aqueous media is preferably one which is palatable to a patient so that they will consume the oral formulation with ease.

When administered to a patient in need thereof in an effective amount, the formulations of the present invention will produce immunosuppression. Preferably, the amount of the pharmaceutical formulation administered is about 0.1 to 10 mg/kg of body weight of the subject per day, more preferably about 0.5 to 3 mg/kg of body weight of the subject per day. The formulation is preferably administered either once a day or twice a day.

When properly administered, the formulations of the present invention may be used for immunosuppression including, for example, to prevent organ rejection or graft vs. host disease, and to treat diseases and conditions, in particular, autoimmune and inflammatory diseases and conditions. Examples of autoimmune and inflammatory diseases contemplated herein include, but are not limited to, Hashimoto's thyroiditis, pernicious anemia, Addison's disease, psoriasis, diabetes, rheumatoid arthritis, systemic lupus erythematosus, dermatomyositis, Sjogren's syndrome, dermatomyositis, lupus erythematosus, multiple sclerosis, myasthenia gravis, Reiter's syndrome, arthritis (rheumatoid arthritis, arthritis chronica progrediente and arthritis deformans) and rheumatic diseases, autoimmune hematological disorder (hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (ulcerative colitis and Crohn's disease) endocrine opthalmopathy, Graves disease, sarcoidosis, primary billiary cirrhosis, juvenile diabetes (diabetes mellitus type 1), uveitis (anterior and posterior), keratoconjunctivitis sicca and vernal keratoconjunctivitis, interstitial lung fibrosis, psoriatic arthritis and glomerulonephritis.

The formulations of the present invention may also be used to treat anti-parasitic, or anti-protozoal diseases such as malaria, coccidiomycosis and schistosomiasis. They may also be used as an agent for reversing or abrogating anti-neoplastic agent resistance in tumors.

The present invention also contemplates a formulation to be administered parenterally (e.g., subcutaneously or intramuscularly). This formulation comprises the following:
a) a pharmaceutically effective amount of $ISA_{Tx}247$;
b) Vitamin E TPGS;
c) MCT oil;
d) Tween 40; and
e) ethanol.

Preferably such a formulation is sterilized prior to administration.

C. Methodology

We have found that stable formulations of the cyclosporin analog $ISA_{Tx}247$ can be prepared. The formulations of the present invention may be prepared in the following manner. However, the person skilled in the art knows that any sequence of these steps is possible. In addition, the amounts of components employed in the following is as detailed above and the methods described below can readily convert one or more steps or completely inverse the process.

While only Formulation 5 details how the microemulsion preconcentrate is added to an aqueous solution to form a microemulsion, any of the microemulsion preconcentrate formulations may be converted to microemulsions by mixing with an aqueous media. Preferably, the preconcentrate is mixed with the aqueous media at a ratio of 1 part preconcentrate to 10–100 parts media. More preferably the aqueous media is apple juice.

Formulation 1

First, the MCT oil is added to the Tween 40 to form a mixture at room temperature (20–25° C.). Next, ethanol is added to the mixture of MCT oil and Tween 40. Next, Vitamin E TPGS is added to the mixture. The mixture is then incubated with stirring at 30–35° C. until clear. Then, the proper amount of $ISA_{Tx}247$ is added. Finally, the ingredients are mixed at 30–35° C. until the $ISA_{Tx}247$ is completely dissolved.

Formulation 2

First, the MCT oil is added to the Tween 80 to form a mixture at room temperature (20–25° C.). Next, ethanol is added to the mixture of MCT oil and Tween 80. Next, Vitamin E TPGS is added to the mixture. The mixture is then incubated with stirring at 30–35° C. until clear. Then, the proper amount of $ISA_{Tx}247$ is added. Finally, the ingredients are mixed at 30–35° C. until the $ISA_{Tx}247$ is completely dissolved.

Formulation 3

First, the MCT oil is added to the Tween 80 to form a mixture at room temperature (20–25° C.). Next, ethanol is added to the mixture of MCT oil and Tween 80. Next, triacetin is added to the mixture. The mixture is then incubated with stirring at 30–35° C. until clear. Then, the proper amount of $ISA_{Tx}247$ is added. Finally, the ingredients are mixed at 30–35° C. until the $ISA_{Tx}247$ is completely dissolved.

Formulation 4

First, the MCT oil is added to the Tween 80 and mixed at room temperature (20–25° C.). Next, isopropyl myristate and ethanol are added to the mixture at room temperature (20–25° C.). Then, the proper amount of $ISA_{Tx}247$ is added. Finally, the ingredients are mixed until the $ISA_{Tx}247$ is completely dissolved at room temperature (20–25° C.).

Formulation 5

First, the MCT oil is added to the Tween 40 to form a mixture at room temperature (20–25° C.). Next, ethanol is added to the mixture of MCT oil and Tween 40. Next, Vitamin E TPGS is added to the mixture. The mixture is then incubated with stirring at 30–35° C. until clear. Then, the proper amount of $ISA_{Tx}247$ is added. Finally, the ingredients are mixed at 30–35° C. until the $ISA_{Tx}247$ is completely dissolved. The resulting preconcentrate is then mixed with aqueous media. Preferably, the preconcentrate is mixed with the aqueous media at a ratio of 1 part preconcentrate to 10–100 parts media.

In preferred methodologies, each of the above formulations are prepared by first dissolving the $ISA_{Tx}247$ in ethanol. The rest of the ingredients may be added in any order.

DISCLOSURE OF THE EXAMPLES OF THE INVENTION

In the examples below, the following abbreviations have the following meanings. If an abbreviation is not defined it has its generally accepted meaning.

| | | |
|---|---|---|
| w/w | = | weight to weight |
| NF | = | National Formulary |
| NF/NP | = | National Formulary/National Pharmacopeia |
| USP | = | United States Pharmacopeia |
| mg | = | milligrams |
| mL | = | milliliters |
| kg | = | kilograms |
| ng | = | nanograms |
| nm | = | nanometers |
| $T_{max}$ | = | Time of maximum concentration |
| $C_{max}$ | = | maximum concentration |
| AUC | = | area under the curve |
| LCMS | = | Liquid Chromatography-Mass Spectrometry |
| MCT | = | Medium chain triglycerides |
| PK | = | Pharmacokinetics |
| PS | = | pig skin |

Two drug products, an oral solution and a soft gelatin capsule, have been developed by Isotechnika, Inc. Both drug products contain a surfactant, ethanol, a lipophilic and/or an amphiphilic solvent as ingredients. Preparation of each is described below.

Example 1

Preparation of $ISA_{Tx}247$ Oral Solution

The following ingredients make up the $ISA_{Tx}247$ drug product-oral solution: $ISA_{Tx}247$, d-alpha Tocopheryl polyethylene glycol 1000 succinate (vitamin E TPGS) NF, Medium Chain Triglycerides (MCT) Oil USP, Tween-40 NF, and 95% Ethanol USP.

TABLE 1

Composition of $ISA_{Tx}247$ Oral Solution

| Ingredient (and Test Standard) | Unit and/or Percentage Formula Strength: 50 mg/mL | Quantity per Batch Lot # 39120228 | Lot # 30010532 | Lot # 30040517 |
|---|---|---|---|---|
| d-alpha Tocopheryl polyethylene glycol 1000 succinate (vitamin E TPGS) NF | 42.24% | 0.16205 kg | 0.544 kg | 0.768 kg |
| Medium Chain Triglycerides (MCT) Oil USP | 21.12% | 0.08102 kg | 0.272 kg | 0.384 kg |
| Tween-40 NF | 21.12% | 0.08102 kg | 0.272 kg | 0.384 kg |
| 95% Ethanol USP | 10.56% | 0.04051 kg | 0.136 kg | 0.192 kg |
| $ISA_{Tx}247$ | 4.95% | 0.01900 kg | 0.0637 kg | 0.090 kg |

TABLE 1-continued

Composition of $ISA_{Tx}247$ Oral Solution

| Ingredient (and Test Standard) | Unit and/or Percentage Formula Strength: 50 mg/mL | Quantity per Batch Lot # 39120228 | Lot # 30010532 | Lot # 30040517 |
|---|---|---|---|---|
| Total | 99.99% | 0.38360 kg | 1.286 kg | 1.818 kg |

Vitamin E TPGS was melted in a hot box and transferred to a liquid dispenser. The warm contents of each TPGS container were mixed for at least one minute to ensure that it was a visually homogeneous liquid. When the temperature of the contents of each barrel was no less than 35° C., a Groen vessel at the required temperature 37.5° C.±2.5° C. was prepared.

The required amount of ingredients Vitamin E TPGS, MCT Oil, Tween 40 and 95% ethanol were weighed in separate vessels properly labeled for identification. The Vitamin E TPGS was immediately transferred into the Groen vessel. The MCT Oil, Tween 40, and ethanol were transferred in a stepwise fashion quantitatively to the vessel containing pre-weighed Vitamin E TPGS. The vessel was securely covered to reduce ethanol evaporation and mixed at 37.5±2.5° C. for 15–20 minutes after the addition of ethanol.

The top and bottom samples were observed using sterile glass disposable pipettes. The pipette contents were expected to be homogeneous and clear when viewed.

The mixer was set so that a slight vortex was achieved. The container was covered to reduce ethanol evaporation during mixing. $ISA_{Tx}247$ was added to the continuously mixing blend. Then the container was sealed. The mixture was checked every half hour until the powder had completely dissolved.

Example 2

Preparation of $ISA_{Tx}247$ Gelatin Capsule

The present invention also contemplates a soft gelatin capsule. This capsule contains $ISA_{Tx}247$ and the same non-medicinal ingredients as the oral solution encapsulated in gelatin type 2D PS(NF/NP) capsules containing gelatin, glycerin, water, and sorbitol.

The $ISA_{Tx}247$ gelatin capsule was prepared by encapsulating the $ISA_{Tx}247$ oral solution (50 mg/mL) comprised of $ISA_{Tx}247$, Vitamin E TPGS NF, medium chain triglycerides (MCT) oil USP, Tween-40 NF, and 95% ethanol USP, into gelatin type 2D PS(NF/NP) capsules. The gelatin type 2D PS(NF/NP) capsules was prepared using gelatin NF (pig skin), glycerin USP, purified water USP, and 76% sorbitol special.

Example 3

Stability/Shelf-life Measurements

The Table below shows stability data, as measured by well known LCMS techniques, for Formulation 1 in both bottled (stored at 30° C.) and soft-gel capsule forms (stored at room temperature). The formulations are stable under normal storage conditions.

TABLE 2

| | ISA$_{Tx}$247 Concentration (mg/mL) | | |
|---|---|---|---|
| | 0 Months | 6 Months | 24 Months |
| Bottled Formulation | 57.1 ± 0.5 | 56.7 ± 0.7 | 58.0 ± 0.6 |
| Soft-gel Capsules | 41.1 ± 0.6 | 42.4 ± 1.0 | 41.4 ± 0.9[A] |

[A]18 month measurement for soft-gel capsules

Example 4

Comparison of Pharmacokinetic (PK) Profiles

The formulations indicated below were given to Sprague Dawley rats by oral gavage and blood levels of ISA$_{Tx}$247 were monitored at regular intervals over time to generate a concentration versus time curve (i.e., pharmacokinetic profile). Below is a comparison of the PK profiles of various ISA$_{Tx}$247 formulations, including those disclosed herein. While group number 2 shows good bioavailability in the rat model, as shown in Table 3, these results may vary substantially in dog or human models (see table 4).

TABLE 3

PK profiles of various ISA$_{Tx}$247 formulations

| Route of Admin. | Group | T$_{max}$ | C$_{max}$ | Half-life | AUC | Bioavailability relative to Group 1 |
|---|---|---|---|---|---|---|
| Oral | 1 | 2 | 49 | 7.3 | 559 | +0 |
| Oral | 2 | 4 | 75 | 6.1 | 1150 | +106 |
| Oral | 3 | 4 | 36 | 18.6 | 491 | −12 |
| Oral | 4 | 4 | 68 | 7.4 | 885 | +58 |
| Oral | 5 | 2 | 104 | 7.1 | 1298 | +132 |
| Oral | 6 | 4 | 57 | 7.7 | 750 | +34 |

Tmax = Time (hours) to maximum blood level of ISA$_{Tx}$247
Cmax = Maximum blood level (ng/mL) of ISA$_{Tx}$247
Half-life = Time (hours) to reach half maximal ISA$_{Tx}$247 blood level
AUC = Area under the curve. (Related to bioavailability of drug.)

Group 1:
VitE-TPGS/MCT Oil/Tween 40/ethanol: 4/2/2/1 (w/w/w/w). (Disclosed herein as Formulation 1).

Group 2:
VitE-TPGS/MCT Oil/Tween 80/ethanol: 2/4/2/1 (w/w/w/w) (Disclosed herein as Formulation 2).

Group 3:
MCT Oil/Tween 80/Triacetin/ethanol: 5/3/1/1 (w/w/w/w) (Disclosed herein as Formulation 3).

Group 4:
Tween 80/VitE-TPGS/ethanol/isopropyl myristate: 2/1/1/6 (w/w/w/w) (Disclosed herein as Formulation 4).

Group 5 (comparative example):
Vit E/propylene glycol/Maisine/Chremophor RH 40/ethanol: 3/1.2/5/6.2/2 (w/w/w/w).

Group 6:
This is the formulation diluted 1:65 in apple juice to form a microemulsion. (Disclosed herein as Formulation 5).

Example 5

Preparation of Microemulsions

Over 100 ratio permutations of formulation components were tested for microemulsion formation (defined as less than 0.1 and 0.01 absorbance at 485 and 900 nm, respectively). Formulations tested included ratios of components from:
5–10% ISA$_{Tx}$247
0–50% Vitamin E-TPGS
0–50% Tween 40 and/or Tween 80
0–50% MCT Oil
5–15% Ethanol.

Less than 20% of the formulations tested produced microemulsions. The microemulsion formation is relatively independent of the ratio of either Vitamin E-TPGS or ethanol. However, formulations with ratio's of Vitamin E-TPGS greater than 50%, and ethanol less than 5%, result in preconcentrates that are frozen at room temperature, which are less preferred. FIG. 1 shows a table for the formation of microemulsion preconcentrates as a function of excipient ratio for Tween 40 and MCT Oil.

Example 6

Comparison of Pharmacokinetic (PK) Profiles in Dogs

FIG. 2 shows a graph providing a comparison of pharmacokinetic (PK) profiles for our ISA$_{Tx}$247 microemulsion in comparison with Neoral®) in Beagle dogs. The data is also tabulated below. The formulations were given to Beagle dogs (n=6) by oral gavage and blood levels of ISA$_{Tx}$247 were monitored at regular intervals over time to generate a concentration versus time curve (i.e., pharmacokinetic profile). Specifically, dogs were given 2 mL of either formulation (100 mg/mL) by oral gavage. Blood was withdrawn at T=0, 0.5, 1, 2.5, 5, 7.5, 12 and 24 hours post-dose and analyzed by Liquid Chromatography—Mass Spectrometry (LCMS).

TABLE 4

Summary of Results

| Route of Administration | Group | Tmax | Cmax | AUC |
|---|---|---|---|---|
| Oral | 1 | 2 H | 1439 ± 378 | 8290 |
| Oral | 2 | 2 H | 2158 ± 677 | 11460 |

Tmax = Time (hours) to maximum blood level of ISA$_{Tx}$247
Cmax = Maximum blood level (ng/ml) of ISA$_{Tx}$247
AUC = Area under the curve. (Related to bioavailability of drug.)

Group 1: Formulation 1: VitE-TPGS/MCT Oil/Tween 40/ethanol: 4/2/2/1 (w/w/w/w).

Group 2: Neoral®

Although these data indicate a slightly lower bioavailability of the ISA$_{Tx}$247 formulation, relative to Neoral, it is substantially greater than the bioavailability provided by Sandimmune®. (Data not shown) Neoral (is generally reported to be about 40% bioavailable. As Table 4 illustrates, the bioavailability of Group number 1 is comparable to that of Neoral®.

These data indicate that the formulations of the present invention may have bioavailability comparable to other formulations of cyclosporin and may reduce adverse effects associated with the administration of cyclosporin.

Example 7

Pharmacokinetic and Toxicokinetic Properties of

ISA$_{TX}$247 and Cyclosporin A

The pharmacokinetic and toxicokinetic parameters of ISA$_{TX}$247 (45–50% of E-isomer and 50–55% of Z-isomer) and cyclosporine A were tested in a rabbit model. The rabbit has also been used as a model to study cyclosporine A nephrotoxicity, but far less frequently than the rat. Studies have found that cyclosporine A administered to the rabbit causes structural and functional changes at a dose not only lower than has been previously reported in other animal models, but also within at least the upper level of the therapeutic range in humans (Thliveris et al., 1991, 1994). Also, the finding of interstitial fibrosis and arteriolopathy, in addition to the cytological changes in the tubules, suggests that the rabbit is a more appropriate model to study nephrotoxicity, since these structural entities are hallmarks of nephrotoxicity observed in humans. ISA$_{TX}$247 was administered intravenously (i.v.) for the first 7 days and subcutaneously (s.c.) for an additional 23 days according to the following schedule.

TABLE 5

The Dose Administration Schedule for the Investigation of the Pharmacokinetic and Toxicokinetic Properties of ISA$_{TX}$247 in the Rabbit Model

| Treatment Group | Days 1–7: i.v. Dose (mg/kg) | Days 8–30: s.c. Dose (mg/kg) | Number of Animals Males | Number of Animals Females |
|---|---|---|---|---|
| 1. Vehicle Control | 0 | 0 | 4 | 4 |
| 2. Cyclosporine A Control | 10 | 10 | 6 | 6 |
| 3. Low-Dose | 5 | 5 | 0 | 2 |
| 4. Medium-Dose | 10 | 10 | 4 | 4 |
| 5. High-Dose | 15 | 15 | 4 | 4 |

Pathogen free rabbits (SPF) were used to ensure any renal changes observed were due to the effect of ISA$_{TX}$247 and not due to pathogens. On Days 1 and 7, blood samples were collected prior to drug administration and at 0.5, 1, 2, 4, 8, 12, 18, and 24 hours post-dose to generate a pharmacokinetic profile. Other evaluated parameters included clinical observations, body weight, food consumption, hematology, clinical chemistry, gross pathology, and histopathological examination of selected tissues/organs.

Blood samples were analyzed via high performance liquid chromatography coupled with mass spectrometry (LCMS). Table 6 below summarizes the average pharmacokinetic parameters in rabbits that received 10 mg/kg of cyclosporine A or ISA$_{TX}$247.

TABLE 6

Pharmacokinetic Parameters of Intravenously Administered Cyclosporine A and ISA$_{TX}$247 in Male Rabbits Receiving 10 mg/kg/day. Results expressed as mean ± SD

| Measured Parameter | Cyclosporine A Day 1 | Cyclosporine A Day 7 | ISA$_{TX}$247 Day 1 | ISA$_{TX}$247 Day 7 |
|---|---|---|---|---|
| t$_{max}$ (hours) | 0.5 | 0.5 | 0.5 | 0.5 |
| C$_{max}$ (@g/L) | 1954 ± 320 | 2171 ± 612 | 1915 ± 149 | 1959 ± 470 |
| t½ (hours) | 7.4 ± 2.8 | 9.0 ± 4.0 | 7.4 ± 1.7 | 9.2 ± 1.1 |
| AUC (@g@hr/L) | 6697 ± 1717 | 6685 ± 1247 | 5659 ± 1309 | 5697 ± 1373 |

There were no statistically significantly differences between the pharmacokinetic parameters of cyclosporine A and ISA$_{TX}$247 in male rabbits receiving 10 mg/kg/day. The pharmacokinetic parameters of ISA$_{TX}$247 in female rabbits receiving the same dose were not significantly different from that observed in the male rabbits, with the exception of maximum concentration on Day 7.

No significant changes were noted in the hematological parameters of rabbits receiving a vehicle control, cyclosporine A, or ISA$_{TX}$247. A difference was noted in the creatinine levels in the various groups over the course of the study, as is shown in Table 7 below. These differences indicated that cyclosporine A had a significantly greater negative effect on the kidneys than either the vehicle control or ISA$_{TX}$247. It should be noted that even at a 50% higher dose, 15 mg/kg/day, as compared to 10 mg/kg/day cyclosporine A, ISA$_{TX}$247 did not result in any significant increase in serum creatinine levels.

TABLE 7

Percent Change in Serum Creatinine Levels Over Baseline in Male Rabbits Receiving Vehicle, Cyclosporine A, or ISA$_{TX}$247 for 30 Days

| Treatment Group | Day 15 | Day 30 |
|---|---|---|
| Vehicle | +6% | −3% |
| Cyclosporine A (10 mg/kg) | +22% | +33% |
| ISA$_{TX}$247 (10 mg/kg) | +1% | +10% |
| ISA$_{TX}$247 (15 mg/kg) | −19% | −11% |

Examination of organs in all rabbits receiving the vehicle control, 10 mg/kg cyclosporine A, 5 mg/kg ISA$_{TX}$247, or 10 mg/kg ISA$_{TX}$247 revealed no significant abnormalities. This was especially true for the kidneys, in which no evidence of interstitial fibrosis, normally seen in cyclosporine A-treated animals (Thliveris et al., 1991, 1994) was noted. In male rabbits that received 15 mg/kg ISA$_{TX}$247, a decrease in spermatogenesis was noted. No changes were noted in the 3 female rabbits that completed the study at this dose of 15 mg/kg ISA$_{TX}$247.

While this invention has been particularly shown and described with references to preferred embodiments thereof, it will be understood by those skilled in the art that various changes in form and details may be made therein without departing from the spirit and scope of the invention as defined by the appended claims.

All references discussed above are herein incorporated by reference in their entirety.

We claim:

1. A pharmaceutical composition comprising:
   a) a pharmaceutically effective amount of ISA$_{Tx}$247;
   b) Vitamin E TPGS;
   c) MCT oil;
   d) an emulsifier; and
   e) ethanol wherein the pharmaceutical composition is a microemulsion or a microemulsion preconcentrate.

2. The pharmaceutical composition of claim 1 wherein the emulsifier is selected from the group consisting of polyoxyethylene(20)sorbitamnonopalmitate and polyoxyethylene(20)sorbitanmonooleate.

3. The pharmaceutical composition of claim 1, which comprises from abut 5 to about 10% by weight of ISA$_{Tx}$247, greater than 0% to about 50% by weight of Vitamin E TPGS, greater than 0% to about 50% by weight of MCT oil, greater than 0% to about 50% by weight of emulsifier and about 5 to abut 15% by weight of ethanol, wherein the composition is a liquid microemulsion preconcentrate at room temperature.

4. The pharmaceutical composition of claim 3, wherein the ratio by weight of $ISA_{TX}247$:Vitamin E TPGS:MCT oil:emulsifier:ethanol is about 0.5–1:4:2:2:1.

5. The pharmaceutical composition of claim 3 wherein the emulsifier is polyoxyethylene(20)sorbitanmonopalmitate and further wherein the preconcentrate, when mixed with an aqueous media in a ratio of about 1 part preconcentrate to about 10 to about 100 parts aqueous media, forms a clear stable microemulsion solution.

6. The pharmaceutical composition of claim 1, wherein the bioavailability of $ISA_{TX}247$ is greater than about 30%.

7. The pharmaceutical composition of claim 1, which is adapted for oral administration.

8. The pharmaceutical composition of claim 1 which further comprises biocompatible polymers as protective colloids, suspension stabilizers or bulking agents, excipients, binders and carriers.

9. The pharmaceutical composition of claim 8, wherein the biocompatible polymer is selected from the group consisting of polyoxyethylene glycolated natural or hydrogenated vegetable oils, polyoxyl castor oils, polyoxyethylene-sorbitan-fatty acid esters, polyoxyethylene-polyoxypropylene block co-polymers, lecithins, propylene glycol mono-and di-fatty acid esters and propylene glycol caprylic-capric acid diester.

10. The pharmaceutical composition of claim 9, wherein the biocompatible polymer is selected from the group consisting of polyoxyethylene(20)sorbitanmonolaurate, polyoxyethylene(20)sorbitanmonopalmitate, polyoxyethylene(20)sorbitantrioleate, polyoxyethylene(20)sorbitanmonostearate, polyoxyethylene(20)sorbitanmonooleate, polyoxeythylene(20)sorbitantristearate, polyoxyethylene(4)sorbitanmonolaurate, polyoxyethylene(4)sorbitanmonostearate, and polyoxyethylene(5)sorbitanmonooleate.

11. A method of producing immunosuppression comprising administering to a subject in need thereof an effective amount of the pharmaceutical composition of claim 1.

12. The method of claim 11, wherein the amount of $ISA_{TX}247$ administered is about 0.5 to 3 mg/kg of body weight of said subject per day.

13. The method of claim 11, wherein the pharmaceutical composition is administered using a schedule selected from the group consisting of once a day and twice a day.

14. The method of claim 11, wherein the pharmaceutical composition is used to treat an inflammatory or autoimmune disease or condition in said subject.

15. A method of increasing the immunosuppressive effects of $ISA_{TX}247$ by preparing the pharmaceutical composition of claim 1.

16. The pharmaceutical composition of claim 1 which is a microemulsion preconcentrate.

17. The pharmaceutical composition of claim 16, which is mixed with an aqueous media in a ratio of about 1 part preconcentrate to about 10 to about 100 parts aqueous media.

18. The pharmaceutical composition of claim 17, wherein the aqueous media is selected from the group consisting of water, fruit juice, tea, milk and cocoa, wherein the fruit juice is not grapefruit juice.

19. The pharmaceutical composition of claim 18, wherein the fruit juice is apple juice.

20. The pharmaceutical composition of claim 7, wherein the oral formulation is encapsulated in a soft gelatin capsule.

21. A method of preparing the pharmaceutical composition of claim 1 comprising mixing the MCT oil, the emulsifier, the ethanol, the Vitamin E TPGS, and the pharmaceutically effective amount of $ISA_{TX}247$ until the $ISA_{TX}247$ is completely dissolved, wherein the composition is a liquid at room temperature.

22. The pharmaceutical composition of claim 1, wherein the pharmaceutical composition comprises from about 5% to about 10% by weight of $ISA_{TX}247$, from about 20% to about 50% by weight of Vitamin E TPGS, from about 5% to about 20% by weight of MCT oil, from about 5% to about 50% by weight of Polyoxyethylene(20)sorbitanmonopalmitate and about 5% to about 15% by weight of ethanol.

23. The pharmaceutical composition of claim 22, wherein the ratio by weight of $ISA_{TX}247$:Vitamin E TPGS:MCT oil:emulsifier:ethanol is about 0.5–1:4:2:2:1.

24. The pharmaceutical composition of claim 1, wherein the pharmaceutical composition comprises from about 5% to about 10% by weight of $ISA_{TX}247$, from about 20% to about 50% by weight of Vitamin E TPGS, from about 5% to about 20% by weight of MCT oil, from about 5% to about 50% by weight of polyoxyethylene(20)sorbitanmonooleate and about 5% to about 15% by weight of ethanol.

25. The pharmaceutical composition of claim 24, wherein the ratio by weight of $ISA_{TX}247$:Vitamin E TPGS:MCT oil:emulsifier:ethanol is about 0.5–1:2:4:2:1.

26. The pharmaceutical composition of claim 1 wherein the emulsifier is polyoxyethylene(20)sorbitanmonopalmitate and further wherein the pharmaceutical composition is suitable for subcutaneous or intramuscular administration.

27. A method of preparing the pharmaceutical composition of claim 1, comprising mixing the MCT oil, the emulsifier, the ethanol, the Vitamin E TPGS, and the pharmaceutically effective amount of $ISA_{TX}247$ until the $ISA_{TX}247$ is completely dissolved.

28. The pharmaceutical composition of claim 1 which is used as a preconcentrate, wherein the preconcentrate when mixed with an aqueous media forms a clear stable microemulsion solution.

29. The pharmaceutical composition preconcentrate of claim 28, wherein the pharmaceutical composition comprises from about 5% to about 10% by weight of $ISA_{TX}247$, from about 20% to about 50% by weight of Vitamin E TPGS, from about 5% to about 20% by weight of MCT oil, from about 5% to about 50% by weight of polyoxyethylene(20)sorbitanmonopalmitate and about 5% to about 15% by weight of ethanol.

30. The pharmaceutical composition preconcentrate of claim 29, wherein the ratio by weight of $ISA_{TX}247$:Vitamin E TPGS:MCT oil:emulsifier:ethanol is about 0.5–1:4:2:2:1.

31. A method of preparing the pharmaceutical composition preconcentrate of claim 28, comprising mixing the MCT oil, polyoxyethylene(20)sorbitanmonopalmitate, the ethanol, the Vitamin E TPGS, and the pharmaceutically effective amount of $ISA_{TX}247$ until the $ISA_{TX}247$ is completely dissolved then mixing the composition into an aqueous medium until a microemulsion preconcentrate solution is formed

UNITED STATES PATENT AND TRADEMARK OFFICE
CERTIFICATE OF CORRECTION

PATENT NO. : 7,060,672 B2
APPLICATION NO. : 10/274419
DATED : June 13, 2006
INVENTOR(S) : Naicker et al.

It is certified that error appears in the above-identified patent and that said Letters Patent is hereby corrected as shown below:

On the Title Page,

Item [*] Notice: Subject to any disclaimer, the term of this patent is extended or adjusted under 35 USC 154(b) by (170) days Delete the phrase "by 170 days" and insert -- by 270 days --

Signed and Sealed this

Seventh Day of October, 2008

JON W. DUDAS
*Director of the United States Patent and Trademark Office*